US010814501B2

(12) United States Patent
Auld et al.

(10) Patent No.: US 10,814,501 B2
(45) Date of Patent: Oct. 27, 2020

(54) ROBOTIC SURGICAL SYSTEM

(71) Applicant: Ethicon LLC, Guaynabo, PR (US)

(72) Inventors: Michael D. Auld, Cincinnati, OH (US); Michael P. Weir, Blanchester, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 16/685,027

(22) Filed: Nov. 15, 2019

(65) Prior Publication Data
US 2020/0156267 A1    May 21, 2020

Related U.S. Application Data

(63) Continuation of application No. 14/941,094, filed on Nov. 13, 2015, now Pat. No. 10,500,739.

(51) Int. Cl.
*B25J 19/00* (2006.01)
*A61B 90/50* (2016.01)
(Continued)

(52) U.S. Cl.
CPC .......... *B25J 19/0025* (2013.01); *A61B 34/30* (2016.02); *A61B 34/37* (2016.02); *A61B 90/50* (2016.02);
(Continued)

(58) Field of Classification Search
CPC ......... A61B 34/30; A61B 34/37; A61B 90/50; A61B 2017/00199; A61B 2017/00411;
(Continued)

(56) References Cited

U.S. PATENT DOCUMENTS 6,791,291 B2    9/2004  Shimizu et al.
7,641,242 B2 *  1/2010  Van Pelt ................. B01L 3/565
                                                                285/384
(Continued)

FOREIGN PATENT DOCUMENTS

WO    2010123578 A1    10/2010
WO    2014151621 A1     9/2014
(Continued)

OTHER PUBLICATIONS

International Search Report and Written Opinion for PCT Application No. PCT/US2016/060904 dated Apr. 4, 2017 (16 pages).

*Primary Examiner* — Adam D Rogers
(74) *Attorney, Agent, or Firm* — Mintz Levin Cohn Ferris Glovsky and Popeo, P.C.

(57) ABSTRACT

Techniques for a surgical system are provided that allow an electromechanical surgical arm to be coupled at a location adjacent to a patient, such as a surgical table. A first mating element can be formed on a support member and it can be in electrical communication with a power source and a controller, and a second mating element can be formed on the electromechanical arm. The first and second mating elements can each have a respective electrical contact, and they can be configured such that mechanical coupling between the first and second mating element causes electrical communication to be established between the first and
(Continued)

second electrical contacts and thus between the electromechanical arm and the power source and the controller. The mating elements can include tolerance elements that allow for some discrepancies between the mating elements while still providing a desired mechanical and electrical connection between the mating elements.

19 Claims, 16 Drawing Sheets

(51) Int. Cl.
*A61B 34/37* (2016.01)
*A61B 34/30* (2016.01)
*A61B 90/57* (2016.01)
*A61B 17/00* (2006.01)

(52) U.S. Cl.
CPC ............... *A61B 2017/00199* (2013.01); *A61B 2017/00411* (2013.01); *A61B 2017/00477* (2013.01); *A61B 2017/00862* (2013.01); *A61B 2034/302* (2016.02); *A61B 2090/571* (2016.02); *A61B 2562/227* (2013.01)

(58) Field of Classification Search
CPC ........... A61B 2017/00477; A61B 2017/00862; A61B 2034/302; A61B 2090/571; A61B 2562/227; B25J 3/00; B25J 9/0096; B25J 15/0408; B25J 19/0025; B25J 19/0033; B25J 19/0041; B25J 19/0045
See application file for complete search history.

(56) References Cited

U.S. PATENT DOCUMENTS

| | | | |
|---|---|---|---|
| 8,831,782 | B2 | 9/2014 | Itkowitz |
| 8,968,333 | B2 | 3/2015 | Yu et al. |
| 9,498,298 | B2 | 11/2016 | Lipow et al. |
| 9,872,738 | B2 | 1/2018 | Weir |
| 9,888,975 | B2 | 2/2018 | Auld |
| 9,931,170 | B2 | 4/2018 | Auld |
| 10,082,631 | B2 | 9/2018 | Lee et al. |
| 10,130,429 | B1 | 11/2018 | Weir |
| 10,485,616 | B2 * | 11/2019 | Auld .................... A61B 34/37 |
| 2004/0243147 | A1 | 12/2004 | Lipow |
| 2006/0149418 | A1 | 7/2006 | Anvari |
| 2007/0038115 | A1 | 2/2007 | Quigley et al. |
| 2007/0142970 | A1 | 6/2007 | Burbank et al. |
| 2009/0202387 | A1 | 8/2009 | Dlugos, Jr. et al. |
| 2012/0158013 | A1 | 6/2012 | Stefanchik et al. |
| 2015/0025549 | A1 | 1/2015 | Kilroy et al. |
| 2015/0366438 | A1 | 12/2015 | Wilson et al. |
| 2017/0135771 | A1 | 5/2017 | Auld et al. |
| 2018/0161109 | A1 | 6/2018 | Overmyer et al. |

FOREIGN PATENT DOCUMENTS

| | | |
|---|---|---|
| WO | 2014151952 A1 | 9/2014 |
| WO | 2015175203 A1 | 11/2015 |

\* cited by examiner

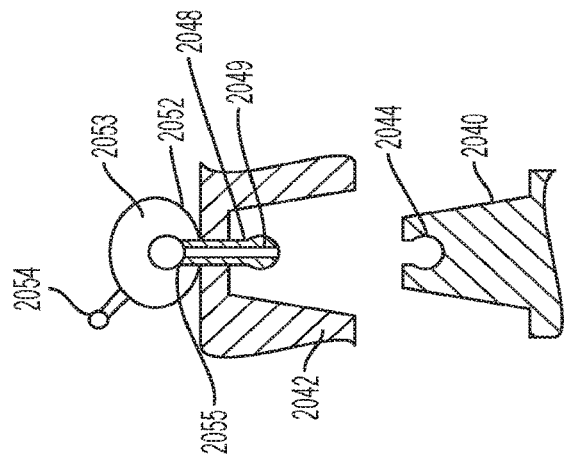
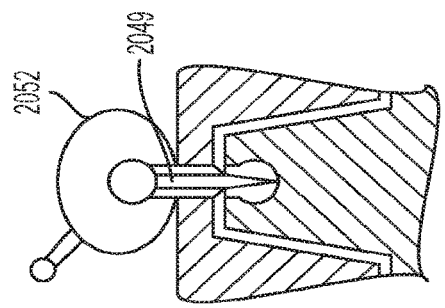
FIG. 24A
FIG. 24B
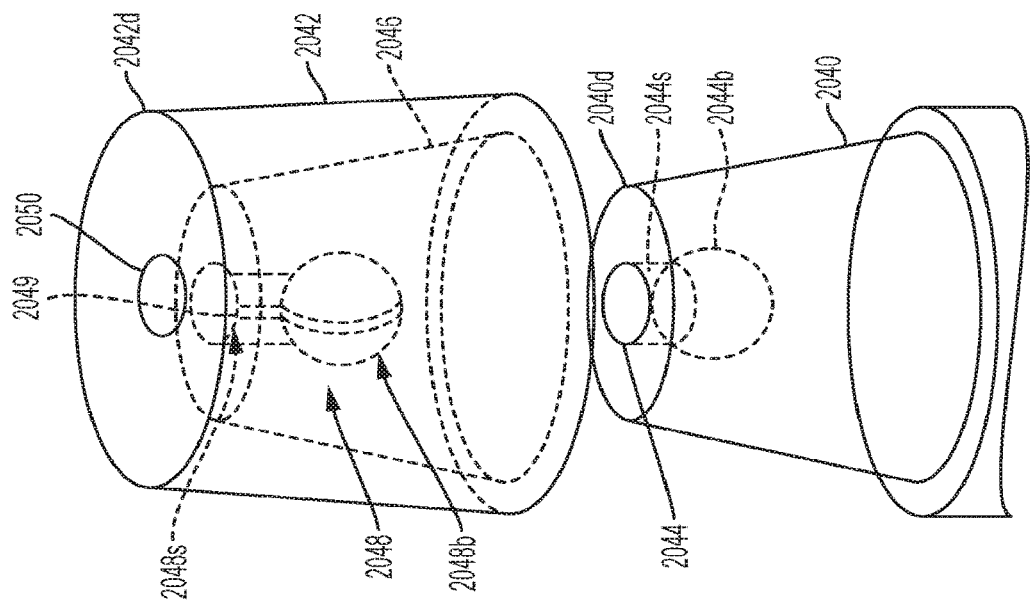
FIG. 23

ROBOTIC SURGICAL SYSTEM

CROSS-REFERENCE TO RELATED APPLICATIONS

The present application is a continuation of U.S. patent application Ser. No. 14/941,094, filed on Nov. 13, 2015, and entitled "ROBOTIC SURGICAL SYSTEM," which is hereby incorporated by reference in its entirety.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. It can be very difficult and expensive to give true force feedback to the surgeon. Another drawback is that robotic systems traditionally only allow the surgeon to control movement of up to two surgical instruments, with any other surgical instruments having to be manually controlled by other medical personnel. It can be difficult for the surgeon and other medical personnel to communicate and synchronize activities of the separately controlled instruments during performance of a surgical procedure.

Accordingly, there remains a need for improved methods, systems, and devices for control of surgical tools in a robotic surgical system.

SUMMARY

In one aspect, a surgical system is provided that in some embodiments includes a support member having a first mating element that is one of a male member and a female receiver, the first mating element having formed thereon a first electrical contact configured to electrically communicate with a power source, and an electromechanical surgical arm having a tool interface configured to receive and support a surgical tool and a second mating element complementary to the first mating element, the second mating element having formed thereon a second electrical contact configured to contact the first electrical contact when the first and second mating elements are mated and to thereby enable electrical communication between the electromechanical arm and a power source through the first electrical contact.

The surgical system can vary in a number of different ways. For example, the electromechanical surgical arm can include an active arm portion configured to receive and support the surgical tool, and a passive arm portion removably coupled to the active portion and having the second mating element formed thereon. The first electrical contact can be in electrical communication with a controller. The first electrical contact can be configured to communicate power and control signals generated by the controller. The controller can be associated with a display providing a user interface for communication with the support member and the electromechanical surgical arm.

In some embodiments, the electromechanical surgical arm can include a mounting pole having the second mating element disposed thereon. The support member can be configured to be removably attached to a surgical table.

The surgical system can further include at least one tolerance element formed on at least one of the first mating element and the second mating element, the at least one tolerance element being configured to provide at least one of axial and radial compliance between the first mating element and the second mating element. The at least one tolerance element can vary in a number of ways. For example, the at least one tolerance element can include at least one deformable element. The at least one deformable element can be or can include a spring. The at least one tolerance element can also be or can include an elastomeric element.

The first and second electrical contacts can be formed such that, when the first and second mating elements are in at least one of axial or radial compliance with respect to each other, the first and second electrical contacts provide the electrical coupling between the support member and the electromechanical arm.

In some embodiments, the surgical system can further include a coupling element configured to secure the first mating element and the second mating element. The coupling element can vary in a number of ways. For example, the coupling element can include a nut. The nut can be attached to at least one of the first mating element and the second mating element via a threaded connection.

The first and second mating elements can be configured to couple to provide the mechanical and electrical coupling between the support member and the electromechanical arm so that a tolerance of the coupling between the first and second mating elements is above a threshold tolerance.

In another aspect, a method of using a surgical system is provided that in some embodiments includes establishing a mechanical and electrical connection between a first mating element formed on a support member having a first electrical contact configured to electrically communicate with a power source and a second mating element having a second electrical contact and formed on an electromechanical surgical arm configured to receive and support a surgical tool, wherein the connection is established such that a mechanical coupling between the first and second mating elements causes electrical connection to be established between the first and second electrical contacts, which causes electrical communication to be established between the electromechanical arm and the power source through the first electrical contact. The method can further include operating the electromechanical surgical arm via the electrical communication established between the electromechanical surgical arm and the power source.

The method can vary in a number of ways. For example, the first mating element can be one of a male member and a female receiver, and the second mating element can be complementary to the first mating element and can be another one of the male member and the female receiver. The electromechanical surgical arm can include an active arm portion configured to receive and support the surgical tool, and a passive arm portion removably coupled to the active portion and having the second mating element formed thereon.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This present disclosure will be more fully understood from the following detailed description taken in conjunction with the accompanying drawings, in which:

FIG. 23 is a perspective view of one embodiment of male and female mating elements;

FIG. 24A is a cross-sectional view of the female mating element of FIG. 23 prior to mating with the male mating element of FIG. 23;

FIG. 24B is a cross-sectional view of the male mating element of FIG. 23 prior to mating with the female mating element of FIG. 23;

DETAILED DESCRIPTION

Figure 1:
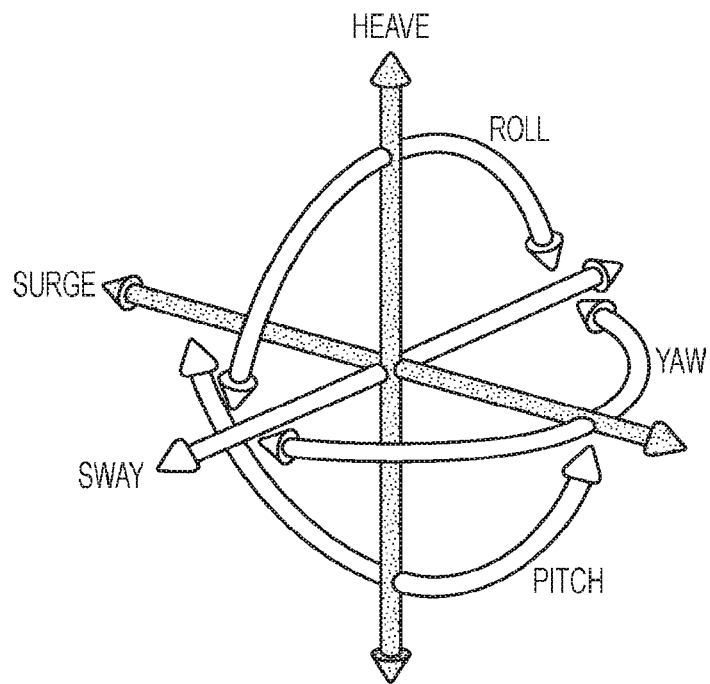
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In some embodiments, systems and techniques are provided for mounting electromechanical surgical arms on a surgical table or other surfaces. The electromechanical surgical arm can have a powered surgical tool coupled thereto and it can be a distinct component that is removably mounted on the surgical table. For example, different electromechanical arms can be required for a useful type of surgery and it can be desired to mount the arms at different places on the surgical table. Also, more than one arm can be used for a surgery. In addition to mechanically attaching an electromechanical arm to a surgical table, electrical power must also be delivered to an active portion (which can be referred to as the "active arm") of the electromechanical arm and to a surgical tool coupled to the arm. If the electromechanical arm is a passive arm, it still must communicate electrical power to the surgical tool coupled thereto. Existing approaches typically involve a step of mechanically coupling the arm to the surgical table and another step of establishing an electrical connection between the arm and the table. However, such procedure can be cumbersome and time-consuming. Moreover, it can be challenging to ensure that various types of electromechanical arms can be securely coupled to a surgical table in a desired manner.

Accordingly, the described systems and techniques provide efficient mechanically coupling of electromechanical arms to a surgical table in a manner such that the mechanical coupling between an arm (or a component to which the arm is coupled) and a table causes electrical connection to be established between the arm and the table. The mechanical and electrical connection in accordance with the described techniques can be established between a mating element coupled to a surgical table and a complementary mating element coupled to an electromechanical arm. The mating elements can be configured to allow an electrical connection therebetween to be made without any additional user input, as a result of establishing the mechanical connection between the mating elements. In this way, assembly and disassembly of a surgical system is simplified.

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the disclosure. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
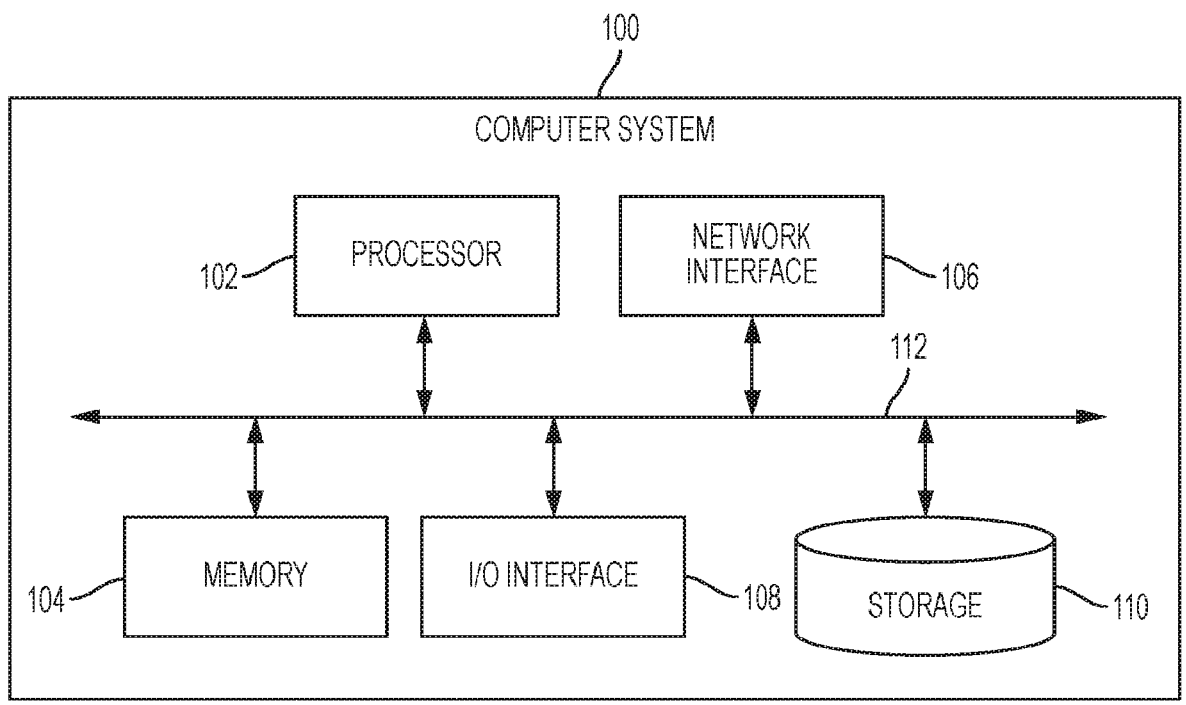
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
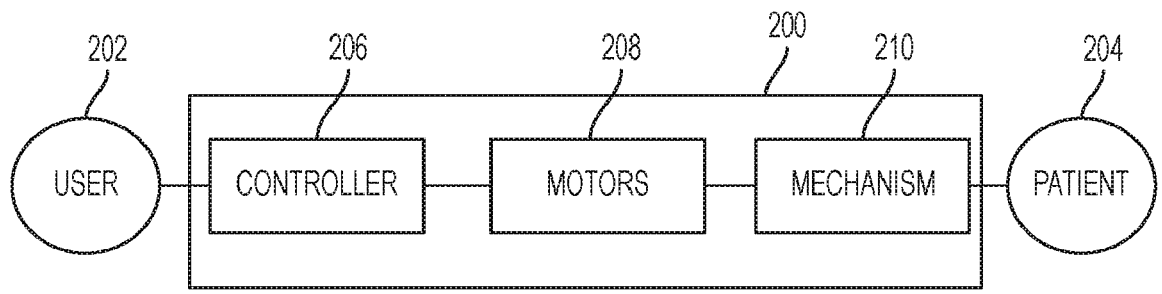
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
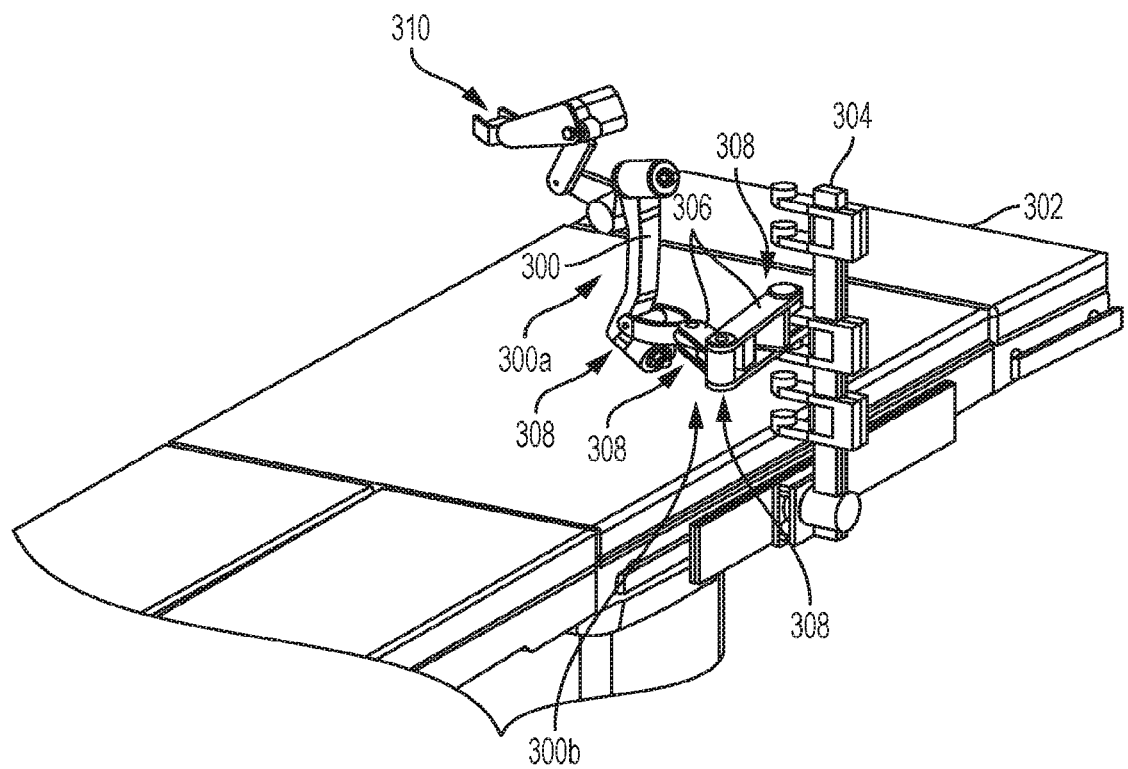
FIG. 4 is a perspective view of one embodiment of an arm of a robotic surgical system, the arm being mounted to a surgical table.
Figure 5:
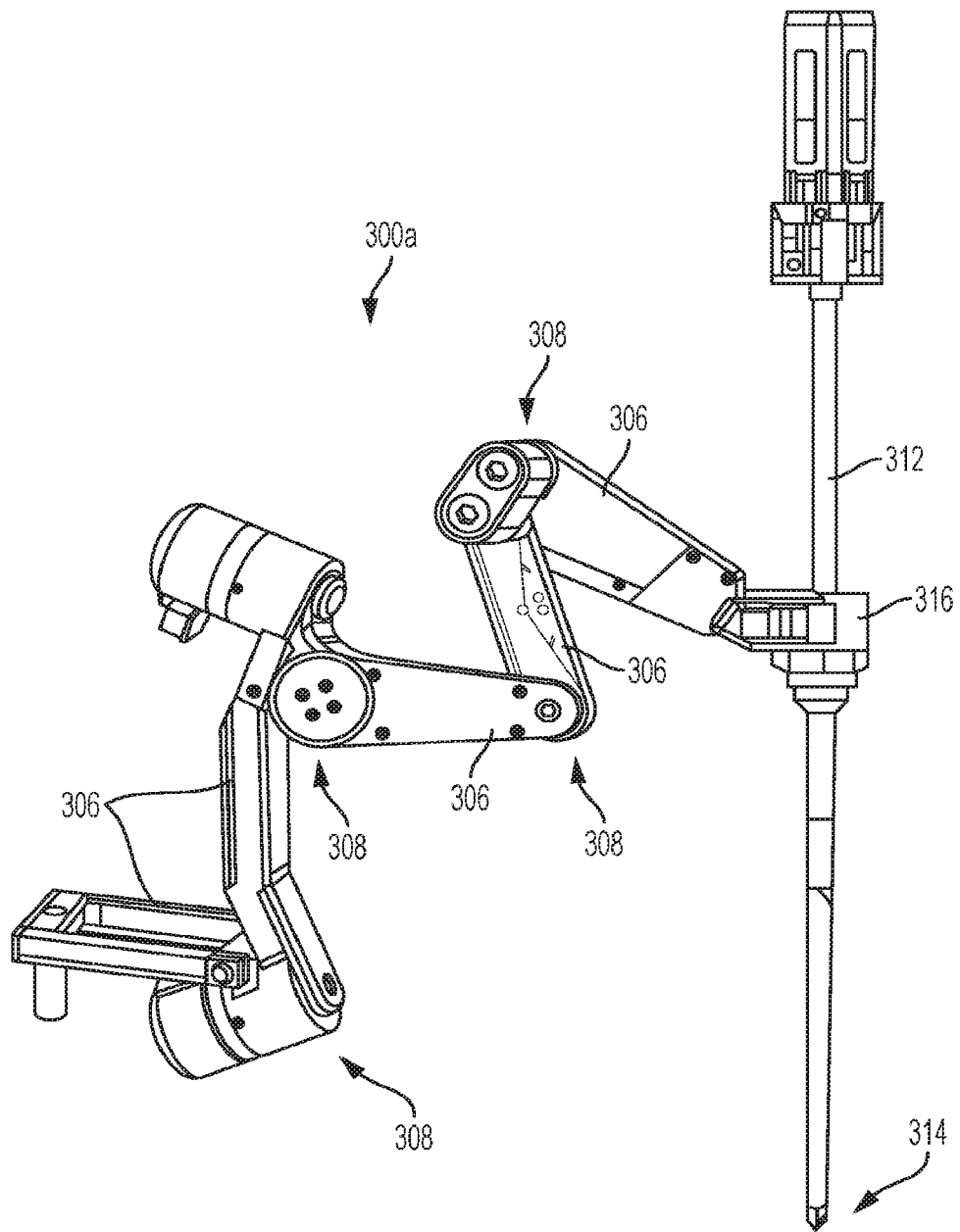
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
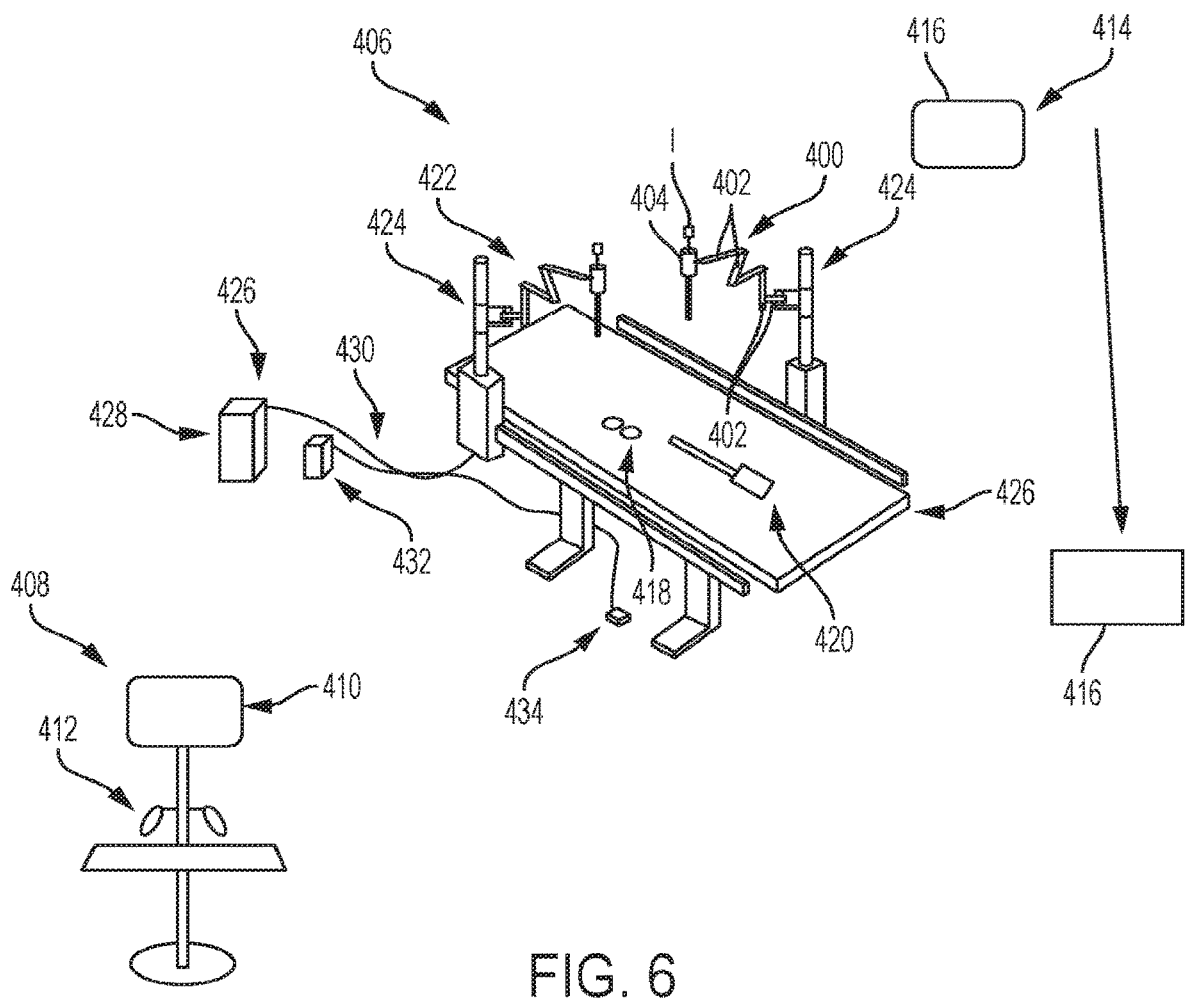
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the arms 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
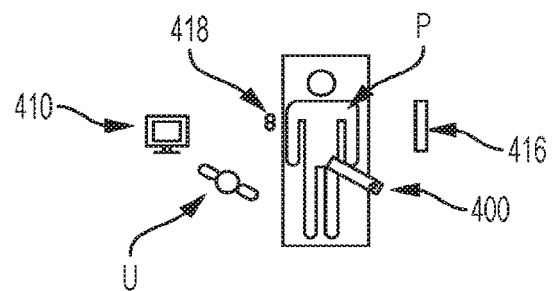
FIG. 7 is a schematic view of one embodiment of the robotic surgical system of FIG. 6 in use during performance of a surgical procedure on a patient.
Figure 8:
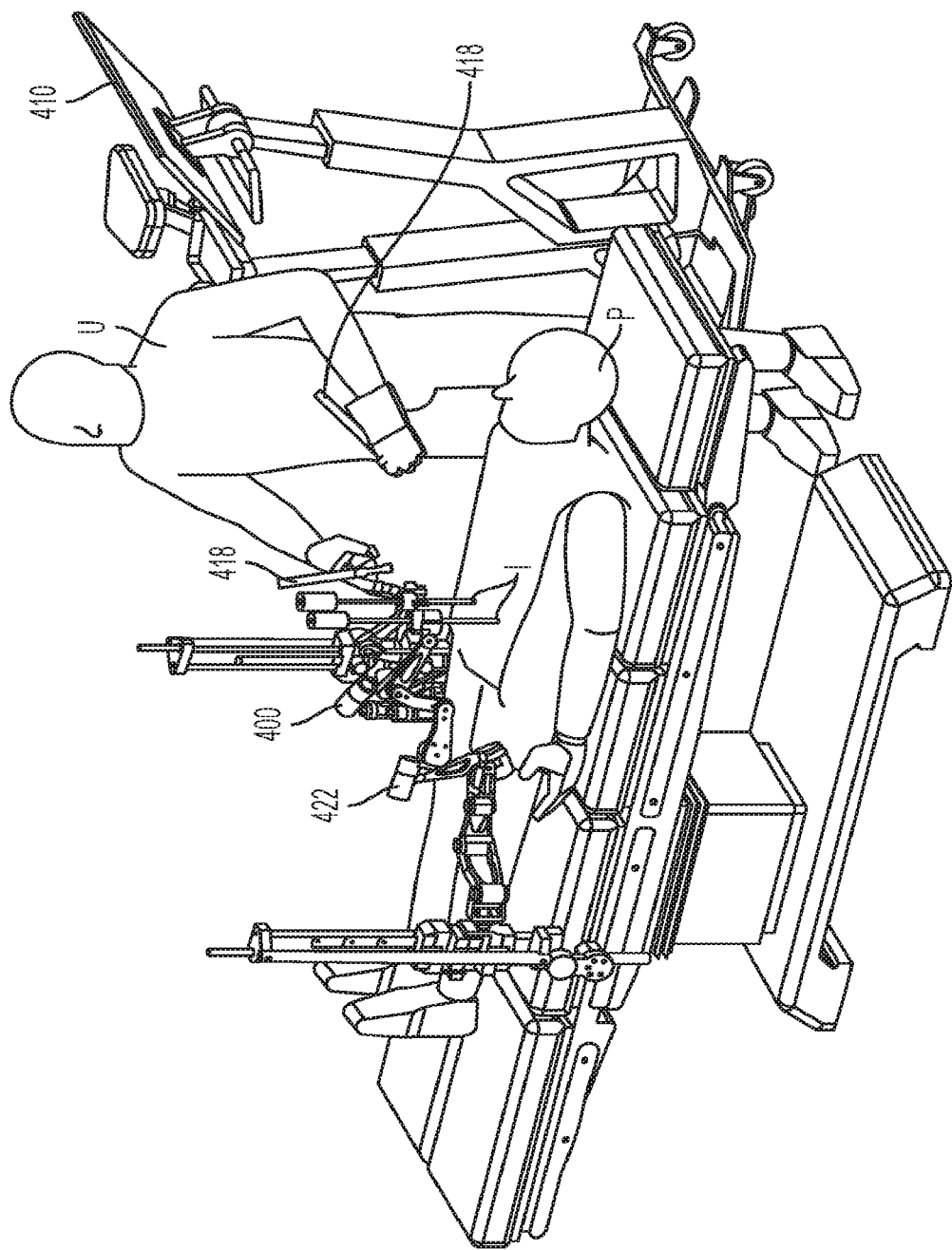
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arms 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
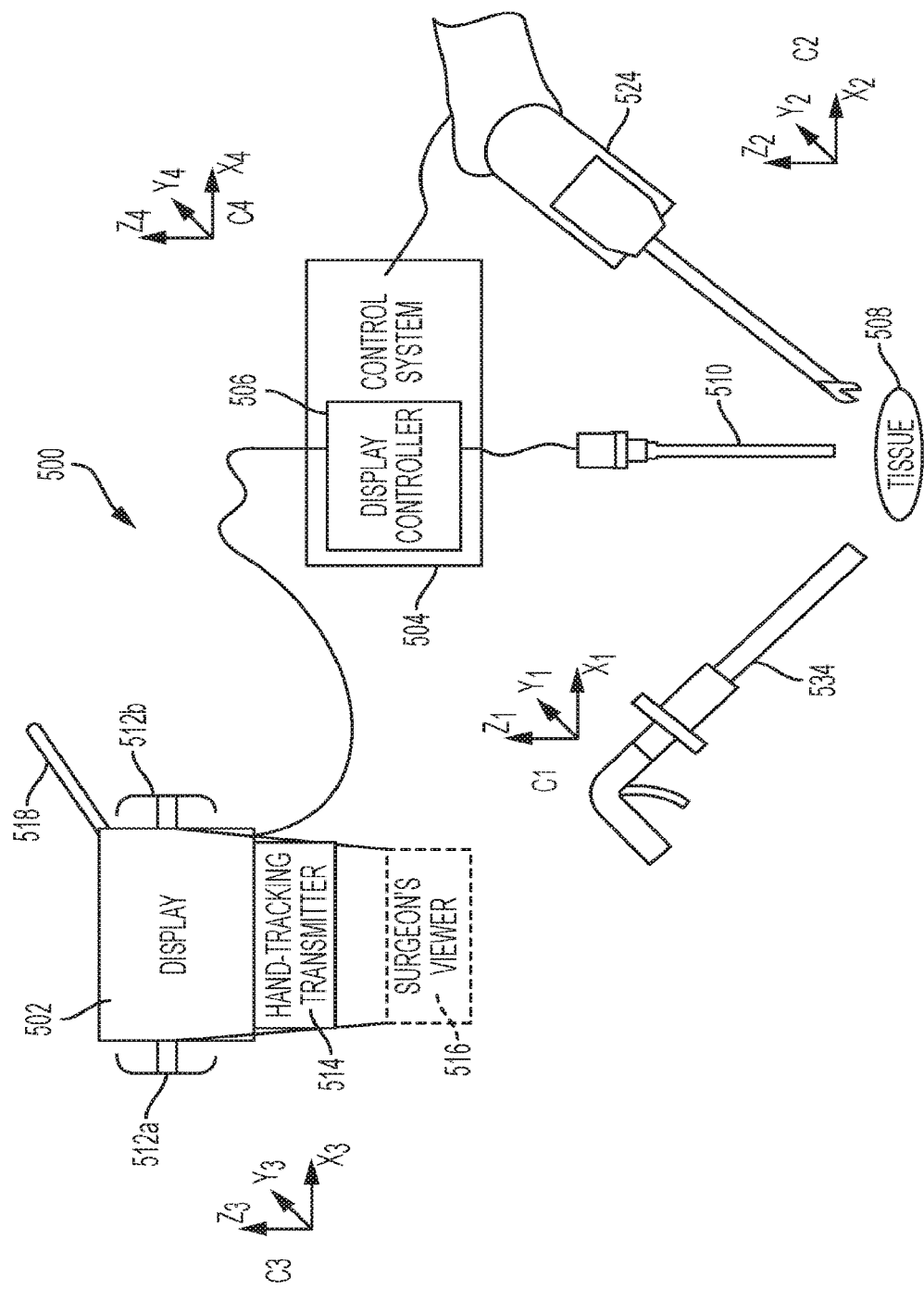
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512*a*, 512*b* configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
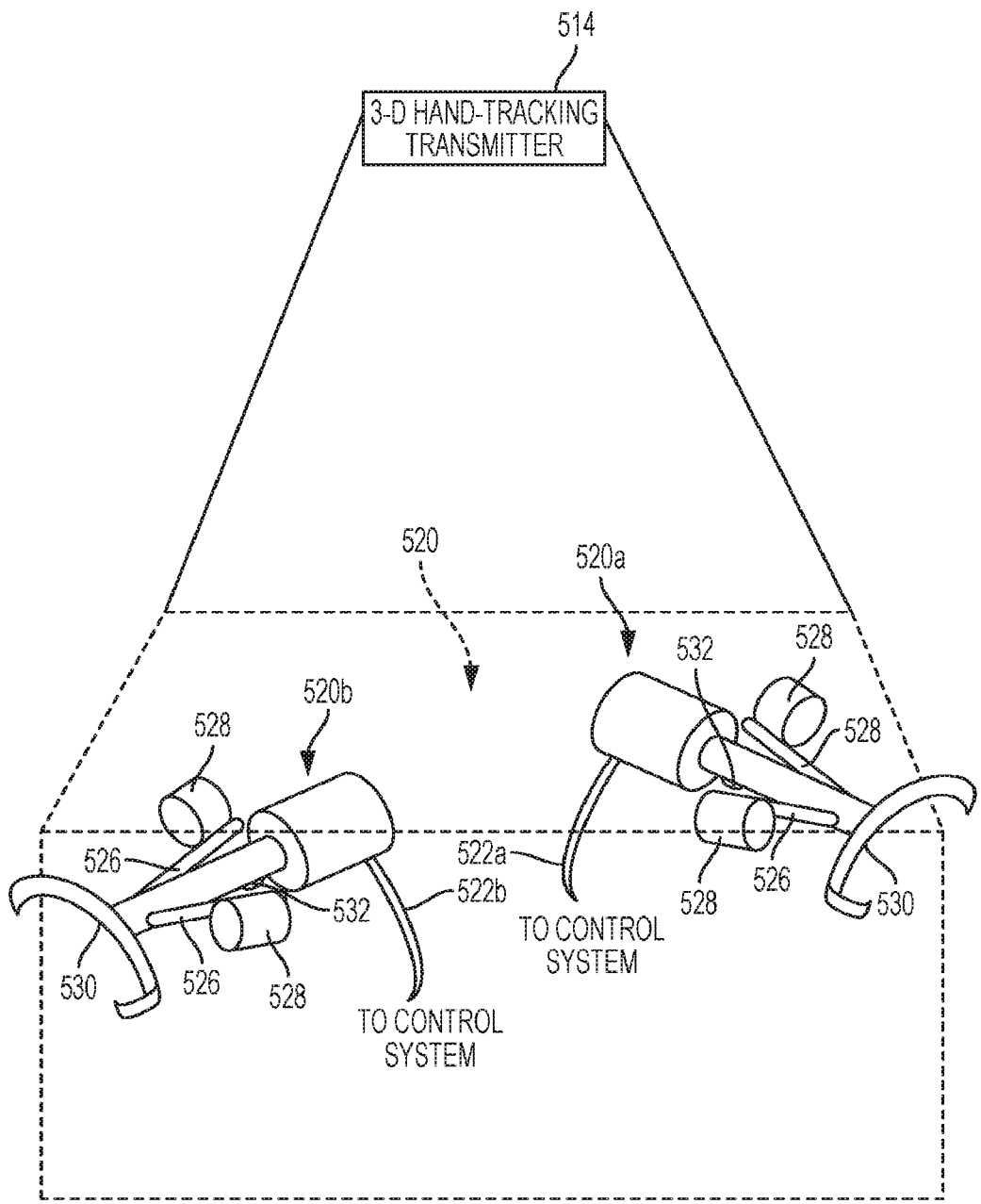
FIG. 10 is a perspective view of one embodiment of a master tool in a field generated by a transmitter of the robotic surgical system of FIG. 9.

Movement of a user-controlled master tool 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522*a*, 522*b*. The control system 504, e.g., a processor thereof, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520*a*, 520*b* that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. The control system 506 can be configured to always orient the display 502 so that the first, second, and third coordinate systems C1, C2, C3 are aligned to the third coordinate system C3. For example, if the user is holding the master tool 520, e.g., one of the first and second master tool grips 520*a*, 520*b*, in one of his/her hands and moves that hand to his/her right, thereby moving the held master tool 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Referring back to FIG. 3, the movement mechanism 210 can include an arm, such as an electromechanical surgical arm. The electromechanical arm can be a passive arm, or it can include both passive and active portions or arms configured as described above. Regardless of its specific configuration, the electromechanical arm can be mounted at a location adjacent to a patient, e.g., to a surgical platform, such as a table, bed, or other platform configured to accommodate a patient and referred to hereinbelow as a "surgical table." Specifically, mating elements formed on an electromechanical arm and components to which the arm is to be mounted provide both mechanical and electrical connections. Accordingly, in some embodiments, the electromechanical arm can be mounted on the surgical table using a mating element formed on the arm and a complementary mating element formed on the table. The mating elements are configured such that a mechanical coupling therebetween enables electrical connection between the mating elements, thus enabling electrical connection between the arm and the table. Electrical contacts can be incorporated into various surfaces of the mechanical connectors or they can be associated with elements disposed on the mechanical connectors. In addition, as described below, the mating elements can be associated with compliance or tolerance elements that allow proper connection to be formed between mating elements even if their configurations do not precisely match. For example, the mating elements can be configured to couple to provide the mechanical and electrical coupling therebetween so that a tolerance of the coupling between is above a certain threshold tolerance. This allows for a simplified, more time- and cost-efficient assembly and disassembly of a surgical system.

Figure 11:
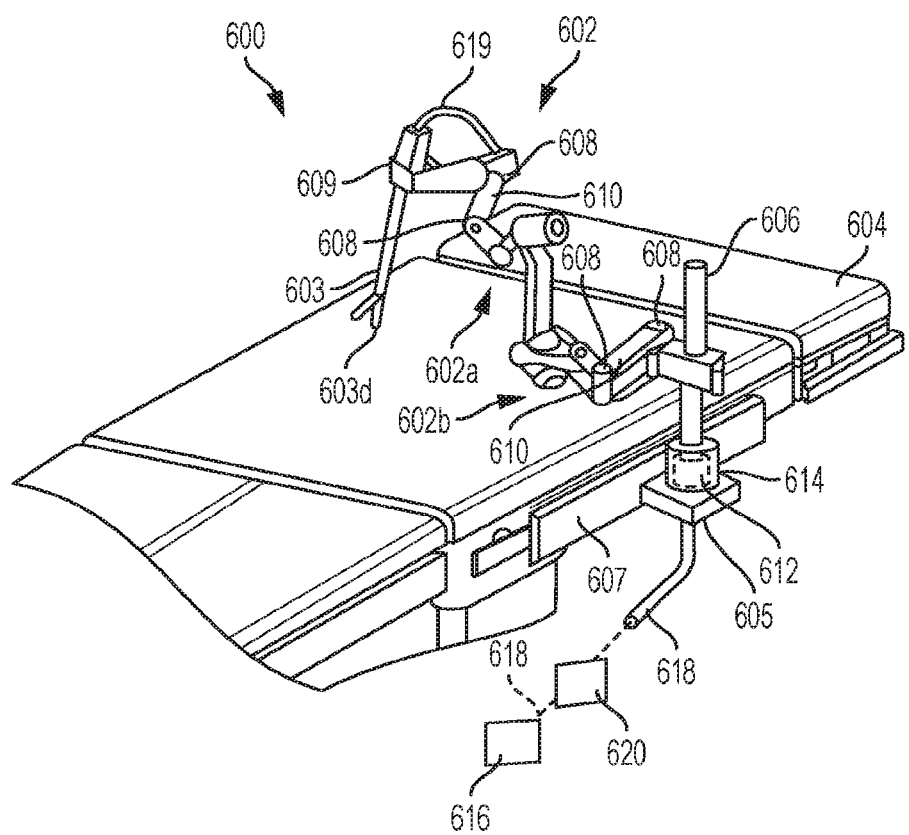
FIG. 11 is a perspective view of one embodiment of an electromechanical surgical arm of a robotic surgical system, the electromechanical surgical arm being mounted to a surgical table.

FIG. 11 illustrates an example of a robotic surgical system 600 including a surgical arm 602 in the form of an electromechanical surgical arm configured to be removably mounted on a surgical table 604. The system 600 can be similar to the system shown in FIG. 4 that includes electromechanical arm 300 mounted to surgical table 302. Thus, as shown in FIG. 11, the electromechanical surgical arm 602 is mounted to the surgical table 604 using a mounting pole or post 606. It should be appreciated, however, that the electromechanical arm 602 can be mounted on the surgical table 604 without the use of the mounting post 606. Furthermore, for the purposes of this description, the mounting post 606 will be considered to be part of the electromechanical surgical arm 602.

The electromechanical surgical arm 602 can include an active portion or arm 602a configured to be actively controlled, e.g., configured to move in response to electronic input, and a passive portion or arm 602b configured to be passively controlled, e.g., configured to move in response to hand or other manual movement thereof. Similar to passive and active portions 300a, 300b of arm 300 in FIG. 4, the passive arm 602b lacks motors or other electrical features, while the active arm 602a includes motors and other electrical features, such as various features associated with the joints, to facilitate electronic control thereof. In at least some embodiments, an arm need not include a passive portion and can be configured to be entirely actively controlled. While the active and passive arms 602a, 602b are sometimes referred to herein as components of a single arm, a person skilled in the art will appreciate that the active arm 602a and the passive arm 602b can be separate arms that are matable to each other.

As illustrated, similar to electromechanical arm 300 in FIG. 4, each of the active and passive arms 602a, 602b includes a plurality of joints 608 coupling mechanical members 610 to each other, some of which are labeled in FIG. 11. It should be appreciated that the electromechanical surgical arm 602 can include any suitable number of the joints 608 and the mechanical members 610 in its active and passive portions, and that the particular implementation of the arm 602 is shown in FIG. 11 is shown by way of example only.

As further shown in FIG. 11, the electromechanical surgical arm 602 is configured to be removably and replaceably coupled to a surgical instrument 603 via a coupling mechanism 609. A distal end 603d of the surgical instrument 603 is configured to be advanced into a body of a patient, e.g., through an incision, through a natural orifice, etc. The instrument's distal end 603d thus includes a working end of the instrument 603 configured to facilitate performance of the surgical procedure within the patient. The distal end 603d can include any type of known end effector, e.g., forceps/graspers, needle drivers, scissors, electrocautery hooks, staplers, clip appliers/removers, suction tools, irrigation tools, etc.

The electromechanical surgical arm 602 is configured to be removably and replaceably coupled to the surgical table 604. In the example of FIG. 11, the passive arm 602b of the electromechanical surgical arm 602 is mounted on the surgical table 604 via the mounting post 606. The surgical table 604 has a first mating element 612 formed on a support member, such as an adapter 605, coupled to the surgical table 604. The electromechanical arm 602 has a second mating element 614 complementary to the first mating element 612. In this example, the second mating element 614 is formed on a proximal end of the mounting post 606 which, as mentioned above, can be part of the electromechanical arm 602. However, it should be appreciated that the second mating element 614 can be formed on the active arm 602a or the passive arm 602b of the electromechanical arm 602. Unless specified otherwise, as used herein, a "proximal" end or portion is referred to an end or portion that is closer to the surgical table or point of anchoring of the electromechanical surgical arm. Also, unless specified otherwise, as used herein, a "distal" end or portion is referred to an end or portion that is farther away from the surgical table or point of anchoring of the electrosurgical arm. Thus, as illustrated, the instrument is distal to the first mating element 612.

In the example illustrated, the first mating element 612 on the surgical table 604 is in the form of a conical male member configured to mate with the corresponding second mating element 614 in the form of a complementary conical female receiver, which is shown transparent in FIG. 11 for illustration purposes only. The conical male element can be distally tapered and it can have any suitable taper angle.

The first and second mating elements 612, 614 are configured to mate to each other such that mechanical coupling therebetween simultaneously provides electrical connection between the first and second mating elements 612, 614. Thus, the electromechanical surgical arm 602 can be coupled to the surgical table 604 via a single connecting action without the need to separately establish mechanical and electrical connections between the arm 602 and the surgical table 604.

The first mating element 612 can be formed on the surgical table 604 in various different ways. In the embodiment of FIG. 11, the first mating element 612 is disposed on the adapter 605 movably coupled to rail 607, which is fixedly coupled to the table 604. The adapter 605 can be repositioned (lengthwise and/or heightwise) along the rail 607 to thereby change a position of the first mating element 612 mated with the second mating element 614. As a result, a position of the electromechanical arm 602 with respect to the surgical table 604 can also be changed.

As discussed in more detail below, the first mating element 612 has formed thereon a first electrical contact configured to electrically communicate with a power source schematically shown in FIG. 11 as a power source 616. Power can be transmitted from the power source 616 to the first mating element 612 via a controller 620 schematically shown in FIG. 11. The controller 620 is configured to provide control signals for controlling operation of the arm 602 (if the arm includes an active portion) and operation of the surgical instrument 603 coupled to the arm 602. The controller 620 can be configured to receive input (e.g., user input or input generated automatically) and generate, based on the received input, control signals relating to operation of the surgical instrument 603 and the arm 602. The controller 620 can also be associated with a display (not shown) providing a user interface for communication with the support member and the electromechanical surgical arm. The display can be configured to render a visual representation of a surgery and/or any other suitable information. The controller 620 can include any other suitable components. Furthermore, in some embodiments, the controller 620 and the power source 616 can be included in the same component.

As shown in FIG. 11, the first mating element 612 electrically communicates with the power source 616 via a cable 618 coupling it to the power source 616 via the controller 620. As also discussed in more detail below, the second mating element 614 has formed thereon a second electrical contact configured to electrically communicate with the first electrical contact on the first mating element 612. The second electrical contact can be coupled to at least one electrical cable 619 configured to transmit electrical power and control signals to the active arm 602a and to the surgical instrument 603 coupled to the electromechanical arm 602. Thus, when electrical connection is established between the first and second mating elements 612, 614, electrical communication is enabled between the electromechanical arm 602, and the controller 620 and the power source 616 through the first electrical contact.

Figure 12:
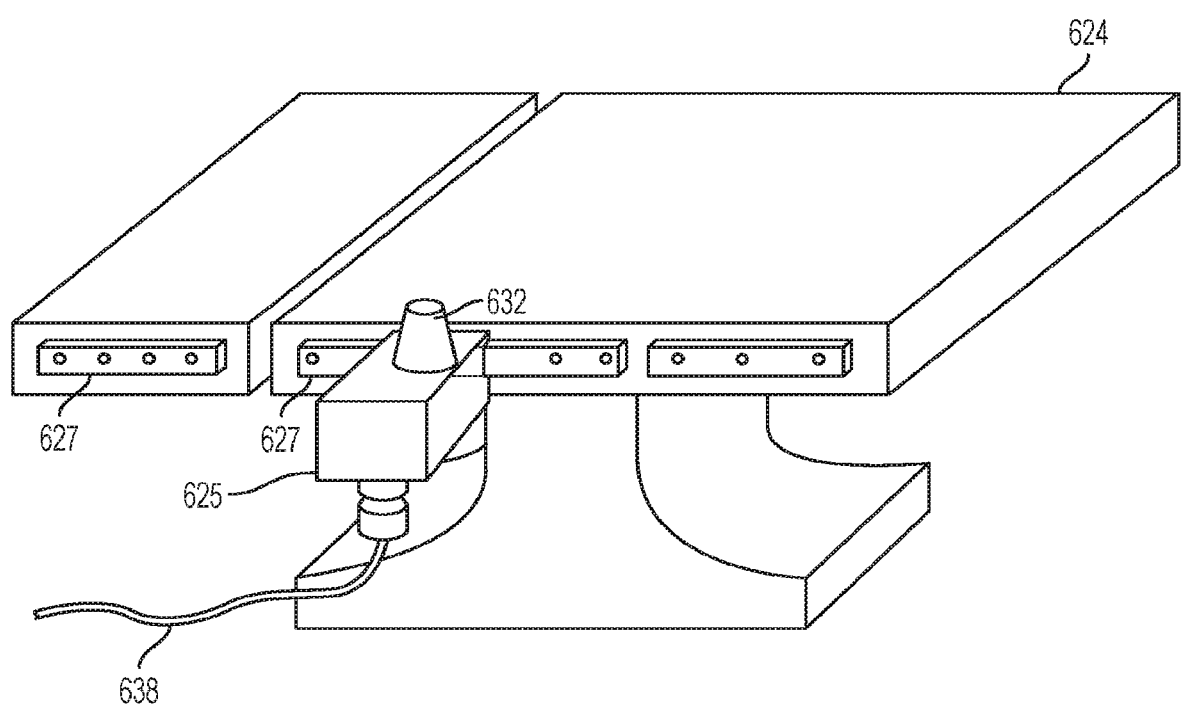
FIG. 12 is a perspective view of one embodiment of a mating element in the form of a male element mountable on a surgical table.

FIG. 12 illustrates another example of a surgical table 624 having a mating element 632 formed thereon. In the example illustrated, the mating element 632 is a male member and is similar to the first mating element 612 shown in FIG. 11. As shown in FIG. 12, similar to the first mating element 612, the mating element 632 is disposed on an adapter 625 movably coupled to a rail 627. The mating element 632 is configured to establish electrical communication with a power source (not shown) via a cable 638 or other wired element. Similar to the example of FIG. 11, the mating element 632 can be configured to receive and transmit control signals from a suitable controller.

The first mating element and complementary second mating element can have a number of different configurations. For example, like in the embodiments of FIGS. 11 and 12, the first mating element can be in the form of a male member configured to mate with a complementary female receiver. The male member can be a conical member that is either tapered or not, a spherical member, or a member having various other shapes (e.g., a cam lock-like member). Furthermore, in some embodiments, the mating element can have configurations different from male and female members (e.g., elements of the same type or similar types), or each of the mating elements can have both female- and male-type of features.

The first and second mating elements can have respective first and second electrical contacts configured to make an electrical connection when the first and second mating elements are mated. Thus, to establish the electrical connection, there is no need to additionally manipulate the mating elements once the mechanical coupling therebetween has made. The electrical contacts can be disposed at various locations on the mating elements and can be configured to maintain electrical contact when the mating elements coupled to one another are rotated or otherwise moved.

The mating elements are configured to be in at least one of radial and axial compliance with one another, depending on a configuration of the elements and electrical contacts formed therein, and additional components that can be associated with the mating elements. The radial and/or axial compliance provides for adequate sealing between the mating elements while allowing for a desired positioning of the mating elements with respect to one another when they are mated. Thus, certain imprecision in the geometry of the mating elements (e.g., due to manufacturing or wear and tear) can be "tolerated" due to the compliance features, and desired mechanical and electrical axial connection can still be achieved between the mating elements.

One or both of the mating elements can have compliance or tolerance elements formed thereon which facilitate establishing of the mechanical and electrical contact between the mating elements. The tolerance elements can be deformable elements, such as, for example, a spring, a push button, or any other type of deformable element. The tolerance elements can also be in the form of an elastomeric element (e.g., a sealing element or other element(s)). In use, the tolerance elements can allow for certain flexibility with respect to positioning of the mating elements with respect to one another.

Also, in the event that there is some variance in the degree to which the mating elements are complementary, the tolerance elements will deform and still allow the mating elements to properly couple to one another both mechanically and electrically. The tolerance elements also allow for interchangeability in use of the mating elements. Thus, in some embodiments, a mating element can sufficiency tightly mate with multiple different other mating elements. For example, a first mating element formed on or associated with a surgical bed (e.g., first mating element 612 in FIG. 11 or first mating element 632 in FIG. 12) can be configured to mate with multiple second mating elements formed on an electromechanical arm, even if the fit between the first element and each of the second mating elements is inexact.

In some embodiments, the mating elements can be configured to couple to provide mechanical and electrical coupling between a point at which the electromechanical arm is anchored (e.g., a support member or other component) and the electromechanical arm so that a tolerance of the coupling between the mating elements is above a certain threshold tolerance. The threshold tolerance can be determined in a number of different ways, and it can depend on a degree to which the mating elements are allowed to differ in their configurations in other aspects.

The compliance or tolerance elements can be distinct elements or they can be part of electrical contacts formed on mating element. Thus, electrical contacts formed on the mating elements can be configured such that they provide mating tolerance (e.g., radial and/or axial). For example, the electrical contacts can be formed by spring-loaded electrical connectors, such as pogo pins or other suitable resilient connectors. The pogo pins can have spherical, rounded or otherwise shaped tips, and they can be disposed on a mating element such that one or more pogo pins make electrical contact with corresponding electrical connectors (e.g., pads or other structures) formed on a complementary mating elements. However, any other suitable types of electrical connectors can be used additionally or alternatively.

Figure 13:
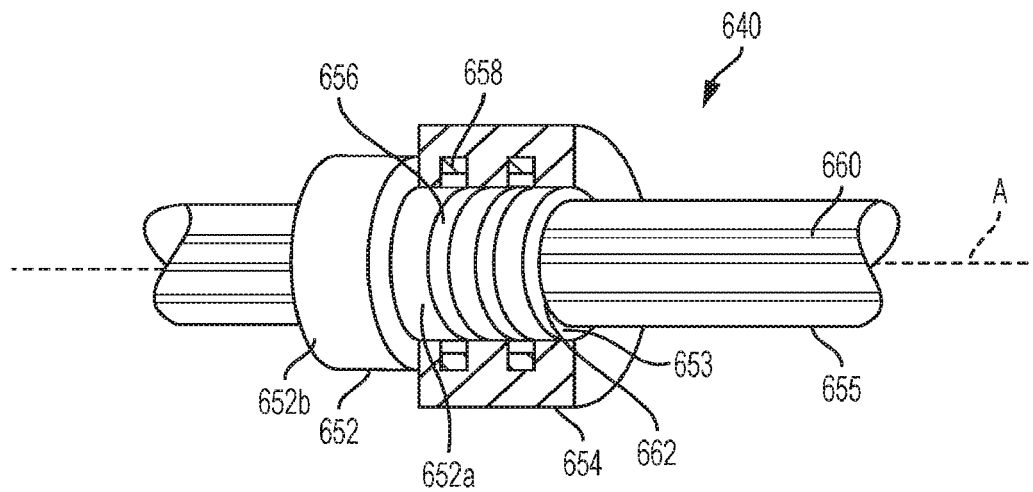
FIG. 13 is a partial cross-sectional view of mating elements configured to provide rotational and translational movements of an electromechanical surgical arm.

FIG. 13 illustrates an example of a connector 640 including a first mating element 652 that can be formed, for example, on a support member coupled to a surgical table (not shown), and a second mating element 654 that can be formed on an electromechanical surgical arm (not shown), which can be a passive or active arm. The first and second mating elements 652, 654 can be configured to form the connector 640 that allows both translational and rotational movements of the electromechanical surgical arm with respect to the surgical table. In the example illustrated, the first mating element 652 is a male member and the second mating element 654 is a type of a female receiver configured to receive therein a portion of the first mating element 652.

As shown in FIG. 13, the first mating element 652 includes first and second portions 652*a*, 652*b* having different diameters such that the first portion 652*a* has a smaller diameter than the second portion 652*b*. As shown, the first portion 652*a* is configured as a cylindrical post extending from the second, also cylindrical, portion 652*b*. The first and second portions 652*a*, 652*b* can be monolithically and/or integrally formed or they can be separate components coupled to each other. The first mating element 652 has an opening 653 formed therethrough that receives therein an adapter in the form of a shaft 655.

The shaft 655 and the first portion 652*a* (and/or other portion(s) of the first mating element 652) are configured such that the first mating element 652 and the shaft 655 do not rotate relative to one another. As shown in FIG. 13, the shaft 655 has line conductors 660 formed along a longitudinal axis A thereof. The shaft 655 is configured to electrically communicate with a power source (not shown), and it can be fixedly coupled to the surgical table and allows electrical current to be transmitted to the first mating element 652 which, in turn, is both mechanically and electrically coupled to the second mating element 654. In this way, electrical current is transmitted to the electromechanical surgical arm having the second mating element 654 disposed thereon. It should be appreciated that three line conductors 660 are shown formed on the shaft 655 by way of example only, as the shaft 655 can include any suitable number of conductors.

The second mating element 654, shown in cross-section in FIG. 13, is shaped, in this example, as a doughnut with an opening and has a diameter that allows it to receive the first portion 652a of the first mating element 652 within its opening. A person skilled in the art will appreciate that the second mating element 654 can have a variety of other shapes and that it can be coupled to the electromechanical arm in a number of different ways.

The first portion 652a of the first mating element 652 can have a first electrical contact formed thereon in the form of circumferential electrodes 656 concentrically formed around its outer surface. Although not shown in FIG. 13, the circumferential electrodes 656 can be configured to electrically communicate with the shaft 655. A person skilled in the art will appreciate that two circumferential electrodes 656 are shown by way of example only, and that any suitable number of electrodes can be formed on the first portion 652a of the first mating element 652.

The second mating element 654 includes a second electrical contact in the form of spring-loaded electrical connectors 658 configured to contact and move along the liner electrodes 656, thus allowing the second mating element 654 to rotate with respect to the first portion 652a of the first mating element 652. The spring-loaded electrical connectors 658 (e.g., pogo pins or other structures) can be equally spaced around the inner wall of the opening formed in the second mating element 654, or they can be positioned in other way(s) so as to be able to contact the circumferential electrodes 656. As shown in FIG. 13, the electrical connectors 658 are formed in rows (with each row including two or more connectors) positioned so that the electrical connectors of one row are electrically matable with one of the linear electrodes 656. Thus, as the second mating element 654 is mechanically coupled with the first mating element 652, electrical communication between the first and second mating elements 652, 654 is established and maintained as the second mating element 654 rotates with respect to the post 652a and therefore with respect to the first mating element 652.

To electrically communicate with the shaft 655, the first portion 652a of the first mating element 652 can have linear electrodes 662, shown partially in FIG. 13, formed on an inner wall of the opening 653. The linear electrodes 662 are configured to abut and move against the linear conductors 660 formed on the shaft 655 such that the first mating element 652 can translate along the shaft 655 while electrical communication therebetween is maintained. The second mating element 654, in turn, can rotate with respect to the first mating element 652. Accordingly, the first and second mating elements 652, 654 form a connection that allows the electromechanical arm to both translate and rotate with respect to the surgical table.

Figure 14A:
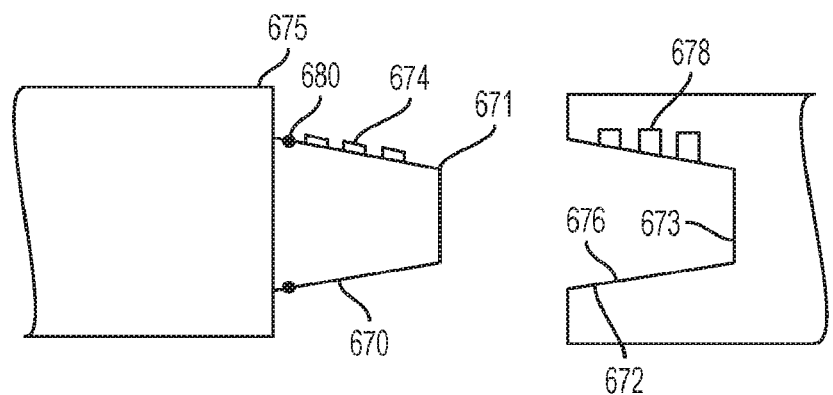
FIG. 14A is a cross-sectional view of one embodiment of male and female mating elements.

FIG. 14A shows an example of a first mating element 670 and a second mating element 672 configured to couple to one other so that mechanical connection therebetween also enables electrical communication between these elements. In the embodiment illustrated, the first mating element 670 is in the form of a male member and the second mating element 672 is in the form of a female receiver. One of the first and second mating elements 670, 672 can be formed on an electromechanical surgical arm and another one of the first and second mating elements 670, 672 can be coupled (e.g., via a support member) to a surgical table or other platform configured to mount the electromechanical surgical arm thereon. For example, the first mating element 670 can be formed on the surgical table and the second mating element 672 can be formed on the electromechanical surgical arm. However, alternatively, the first mating element 670 can be formed on the electromechanical surgical arm and the second mating element 672 can be formed on the surgical table. The first and second mating elements 670, 672 are configured to rotatably mate to one another.

In the embodiment of FIG. 14A, the first mating element 670 is in the form of a conical member that is tapered towards its top portion 671. A base 675 on which the conical member 670 is disposed can be a separate component (e.g., a suitable support member). Alternatively, the base 675 or a portion thereof can be part of the first mating element 670. As shown in FIG. 14A, the first mating element 670 has electrodes 674 formed on an outer surface thereof. The electrodes 674, which form a first electrical contact, can be in the form of linear conductive pads concentrically disposed around the entire surface of the first mating element 670, or they can be formed over a portion of that surface. It should be appreciated that three electrodes 674 are shown in FIG. 14A by way of example only, as any suitable number of electrodes can be formed.

The second mating element 672 is in the form of a female member of a suitable shape having a cavity 676 that can be complementary in shape and size to the first mating element 670. Thus, as shown in FIG. 14A, the cavity 676 has a conical shape that is tapered towards its bottom end 673 that is configured to receive the top portion 671 of the first mating element 670 when the first and second mating elements 670, 672 are coupled to one another. The second mating element 672 has leaf spring or spring-loaded connectors 678 formed on the inner wall of the cavity 676 in a manner complementary to the way in which the electrodes 674 are formed on the conical surface of the first mating element 670. The spring connectors 678 can be formed around the entire perimeter of the cavity 676 or around only a portion thereof. The spring connectors 678 can be arranged in one or more rows so as to form an array, where each row can include two or more spring-loaded connectors.

When the first and second mating elements 670, 672 are mated, the spring connectors 678 make electrical contact with the electrodes 674 throughout rotation of the first and second mating elements 670, 672 with respect to each other.

In the embodiment of FIG. 14A, the first mating element 670 also includes a sealing element 680 that prevents dirt, fluids, and other potential contaminants from entering into the cavity 676 of the second mating element 672 when the first and second mating elements 670, 672 are mated to one another. A person skilled in the art will appreciate that the sealing element 680 may not be present, or that other types of sealing elements can be used additionally or alternatively.

Figure 14B:
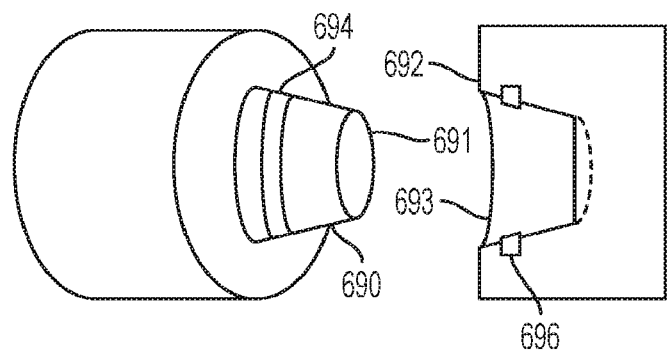
FIG. 14B is a cross-sectional view of another embodiment of male and female mating elements.

FIG. 14B illustrates first and second mating elements 690, 692 similar to the first and second mating elements 670, 672 shown in FIG. 14B. The first mating element 690 is a conically-shaped male member tapered towards its top or distal end 691, and having an electrode 694 forming a first electrical contact and disposed cicrumferentially therearound. The second mating element 692 is in the form of a female receiver having a cavity 693 complementary to the first mating element 690. As shown in FIG. 14B, the second mating element 692 has spring-loaded electrical connectors 696 (e.g., pogo pins or other connectors) disposed on the inner wall of the cavity 693 and forming a second electrical contact. The connectors 696 are configured to abut and move along the electrode 694 such that, when the first and second mating elements 690, 692 are mated to one another electrical communication between the electrode 694 and the connectors 696 is established. The thus established electrical communication is maintained when the first and second mating elements 690, 692 rotate with respect to one another. It should be appreciated that one electrode 694 and respective connectors 696 are shown by way of example only, as the first and second mating elements 690, 692 can have any suitable number of electrodes.

Figure 15:
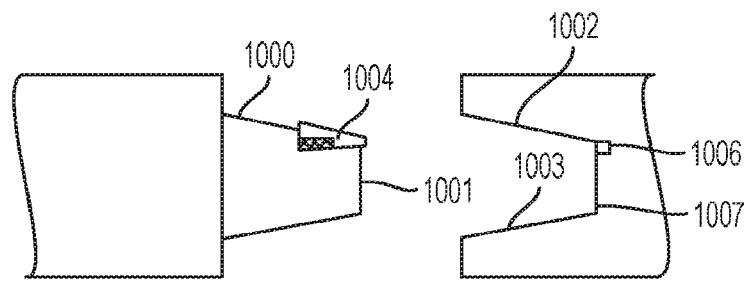
FIG. 15 is a cross-sectional view of another embodiment of male and female mating elements.

In the embodiments shown above in FIGS. 14A and 14B, the connection between first and second mating elements can be described as a radial connection. FIG. 15 illustrates another embodiment of first and second mating elements 1000, 1002 configured to form a connector in accordance with the described techniques. In this example, a connection between the first and second mating elements 1000, 1002 is more linear than in the examples shown in FIGS. 14A and 14B. The first mating element 1000 is a conically-shaped male member tapered towards its top or distal end 1001, and having, at the distal end 1001, a spring-loaded electrical connector 1004 that forms a first electrical contact. The second mating element 1002 is in the form of a female receiver having a cavity 1003 complementary to the first mating element 1000. As shown in FIG. 15, the second mating element 1002 has an electrode 1006 disposed at a base 1007 of the cavity 1003 and forming a second electrical contact. The spring-loaded electrical connector 1004 and the electrode 1006 are configured to establish and maintain electrical connection therebetween when the first and second mating elements 1000, 1002 are mated, and possibly rotated or otherwise manipulated, with the electrical connection being maintained independent of a rotation angle between the first and second mating elements 1000, 1002. It should be appreciated that one electrical connector 1004 and one respective electrode 1006 are shown by way of example only, as the first and second mating elements 1000, 1002 can have any suitable number of electrical connectors forming the first and second electrical contacts.

Figure 16:
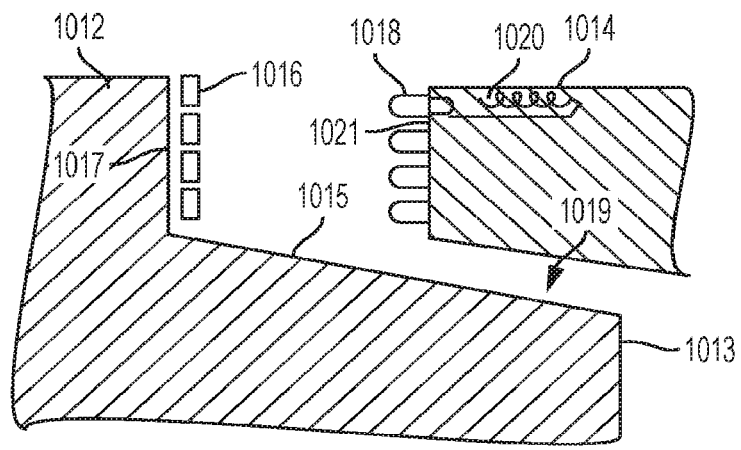
FIG. 16 is a cross-sectional view of another embodiment of male and female mating elements.

FIG. 16 illustrates another embodiment of first and second mating elements 1012, 1014 having electrical connectors incorporated therein. As shown, the first mating element 1012 in the form of a conical male member has electrical connectors 1016 disposed on a base portion 1017 not occupied by a cone portion 1015 of the male member. The base portion 1017 of the first mating element 1012 can be a substantially flat portion of the first mating element 1012 having the cone 1015 extending distally therefrom. The cone portion 1015, shown partially in FIG. 16, can distally taper towards its top or distal end 1013. The connectors 1016 can be in the form of, for example, connector rings or other types of connector elements concentrically disposed along the base portion 1017 to thereby form a first electrical contact.

The second mating element 1014 in the form of a female receiver having a cavity 1019 formed therein. Electrical connectors 1018, forming a second electrical contact of the second mating element 1014, are disposed outside the cavity 1019, as shown in FIG. 16. Specifically, in the example illustrated, the electrical connectors 1018 are disposed on a substantially flat surface 1021 of the second mating element 1014 that faces and abuts the base portion 1017 of the first mating element 1012 when the first and second mating elements 1012, 1014 are mated, as shown in FIG. 16.

The electrical connectors 1018 are complementary to the electrical connectors 1016 formed on the first mating element 1012, and are configured to mate with the electrical connectors 1016 to make electrical connection. The electrical connectors 1018 can be in the form of spring-loaded connectors, such as pogo pins or other electrical connectors. Thus, as shown in FIG. 16 for one of the connectors 1018, each of the connectors 1018 is associated with a spring 1020. However, a person skilled in the art will appreciate that the electrical connectors 1016 and the electrical connectors 1018 can have any suitable configurations that allow them to establish and maintain electrical connection when the first and second mating elements 1012, 1014 are mated. Also, electrical connectors 1016 and four respective spring-loaded electrical connectors 1018 are shown by way of example only, as any number of connector elements can be utilized (e.g., one, two, three, or greater than four) and the described techniques are not limited in this respect. As another variation, the connector elements can be disposed on the distal end 1013 of the first mating element 1012 and on the bottom (not shown) of the cavity 1019, or in other portions of the first and second mating elements 1012, 1014.

In some embodiments, as mentioned above, in addition to electrical connectors, one or both of first and second mating elements can include various compliance or tolerance elements. The tolerance elements can accommodate for wear and tear, dirt, and manufacturing differences between the mating elements and thus can ensure a reliably tight connection between the mating elements. Also, the tolerance elements can allow adequate contact between the mating elements be established even if a mechanical coupling between the mating elements is not precise. The tolerance elements can have a number of various shapes and sizes and they can be disposed in various ways on one or both of first and second mating elements in accordance with the techniques described herein.

Figure 17A:
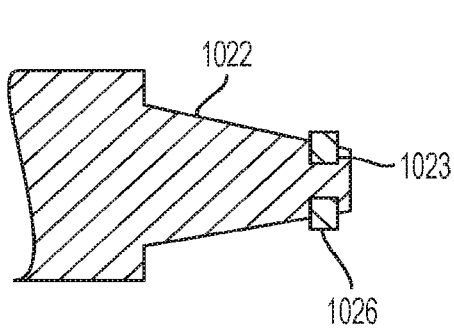
FIG. 17A is a cross-sectional view of one embodiment of a male mating element having axial compliance elements formed thereon.
Figure 17B:
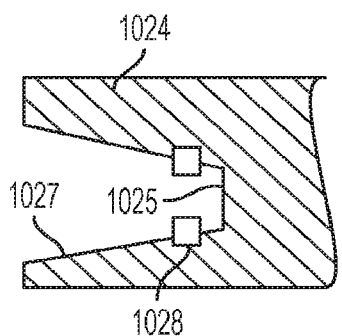
FIG. 17B is a cross-sectional view of one embodiment of a female mating element having axial compliance elements formed thereon.

FIGS. 17A and 17B illustrate an example of tolerance elements that can be disposed on a mating element in the form of a male member (FIG. 17A) and on a mating element in the form of a female receiver (FIG. 17B). In these examples, the tolerance elements shown are radial tolerance elements. It should be appreciated that, although electrical connectors are not shown in FIGS. 17A and 17B, they can be associated with the tolerance elements or can be disposed in other locations of the mating elements.

As shown in FIG. 17A, the mating element 1022, in the form of a male member having a conical tapered shape, has compliance elements 1026 formed on a top end thereof 1023. The mating element 1024 in the form of a female receiver has tolerance elements 1028 formed around a base or bottom 1025 of its cavity 1027, as shown in FIG. 17B. The tolerance elements 1028 may or may not be offset from the bottom 1025 of the cavity 1027. Each of the tolerance elements 1026, 1028 can be formed around entire circumferences of the male mating element 1022 and the cavity 1027 of the female mating element 1024, respectively. Also, the mating element 1022, 1024 can have more than one tolerance element. Furthermore, in some embodiments, each of the tolerance elements 1026, 1028 can be in the form of two or more segments, patches, or other elements disposed around circumferences of the male mating element 1022 and the cavity 1027 of the female mating element 1024, respectively. In some embodiments, only one of the mating elements 1022, 1024 can have tolerance elements whereas another one of the mating element 1022, 1024 can lack tolerance elements. However, it should be appreciated that, in some implementations, both of the mating elements 1022, 1024 can have one or more tolerance elements.

Figure 18:
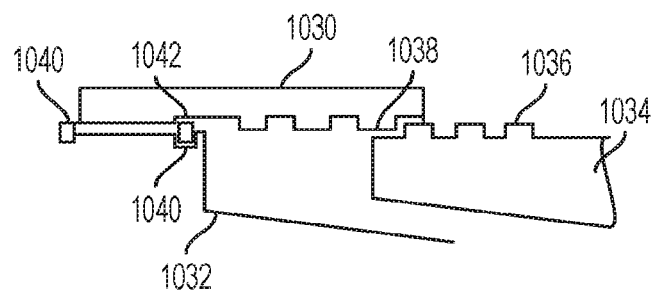
FIG. 18 is a cross-sectional view of one embodiment of male and female mating elements and a coupling element configured to hold the male and female mating elements together.

In some embodiments, a coupling element can be additionally used to reversibly secure first and second mating elements together. The coupling element can be, for example, in the form of a coupling nut. However, other configurations, such as a sleeve or other coupling elements, can also be used. FIG. 18 illustrates schematically an example of a coupling element in the form of a coupling nut 1030 configured to couple a first mating element 1032 in the form of a male member and a second mating element 1034 in the form of a female receiver. The coupling nut 1030 can be lockingly attached to the first and second mating elements 1032, 1034 in a number of ways. For example, in the illustrated embodiment, the second mating element 1034 has a thread 1036 formed on the outer surface thereof and configured to threadably mate with a corresponding thread 1038 formed on the coupling nut 1030. Additionally or alternatively, one or more matable tracks can be formed on the second mating element 1034 and the coupling nut 1030.

The first mating element 1032 can have securing elements 1040 (e.g., securing rings or other elements) configured to lockingly mate with respective securing elements 1042 formed on the coupling nut 1030. It should be appreciated, however, that the first mating element 1032 can have any other elements that allow the coupling nut 1030 to lockingly mate therewith. For example, the first mating element 1032 can include one or more threads or tracks.

In the embodiment of FIG. 18, the coupling nut 1030 rotates but does not move axially with respect to the first mating element 1032, and it engages the thread 1036 of the second mating element 1034. However, as a person skilled in the art will appreciate, the coupling nut can have a variety of other configurations, and the first and second mating elements can have a number of various features that allow the coupling nut to securely hold the first and second mating elements together. Regardless of the specific manner in which the coupling element, such as a coupling nut or other type(s) of element(s), reversibly locks the first and second mating elements together, the coupling element can provide additional security to the mechanical and electrical connections formed between the first and second mating elements. In some embodiments, various sealing elements can be used in addition to the coupling element, to provide venting to the connection between the mating elements and to prevent fluids and/or dirt from interfering with the quality of the connection.

Figure 19:
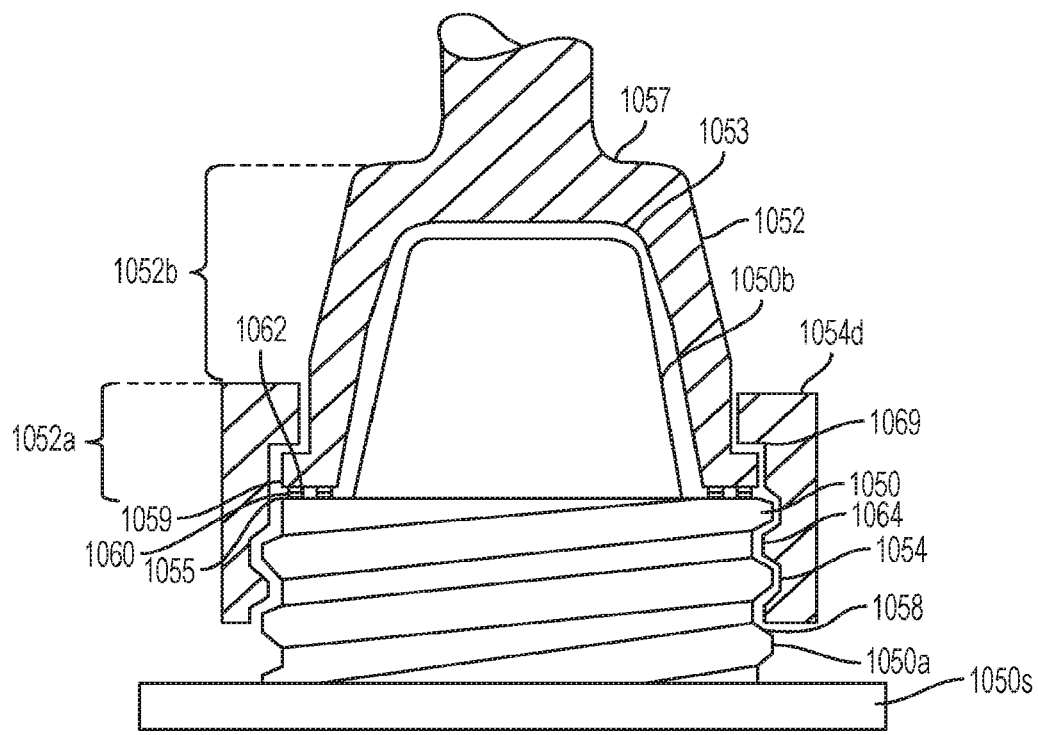
FIG. 19 is a cross-sectional view of another embodiment of male and female mating elements and a coupling element configured to hold the male and female mating elements together.

FIG. 19 illustrates an embodiment of a first mating member 1050 and a second mating element 1052 configured to reversibly mate with the first mating member 1050 and to couple with a coupling member 1054 configured to bring the first and second mating elements 1050, 1052 into a mating position. The first and second mating elements 1050, 1052 can be similar to first and second mating elements 612, 614 (FIG. 11). As shown, the first mating element 1050 is in the form of a male member and includes a bottom or proximal portion 1050a, a top or distal portion 1050b, and a proximal-most support portion 1050s. The proximal, distal, and support portions 1050a, 1050b, 1050s can be integrally and/or monolithically formed or one or more of them can be separate components nonremovably attached to one another in a suitable way.

The proximal portion 1050a has a larger circumference than the distal portion 1050b and is disposed on the support portion 1050s. The support portion 1050s can be coupled to a suitable support member such as, for example, an adapter coupled to a surgical table. Furthermore, in some embodiments, the support portion 1050s can be omitted.

In the illustrated embodiment, the proximal portion 1050a of the first mating member 1050 has an outer thread 1058 disposed around the circumference thereof. The thread 1058 can be an angular thread or other types of thread(s). The distal portion 1050b of the first mating member 1050 can be a conical member extending from a distal-most surface 1055 of the proximal portion 1050a and tapered distally, as shown in FIG. 19. Like in the example illustrated in FIG. 19, the distal portion 1050b can lacks threads. However, in some implementations, it can include one or more threads.

The second mating element 1052 is a female receiver configured to receive in an inner cavity 1053 thereof the distal portion 1050b of the first mating member 1050, as shown in FIG. 19. As shown in FIG. 19, an outer surface 1057 of the second mating element 1052 can have a bottom or proximal portion 1052a that is tapered proximally (or it may not taper) and that includes a stepped element 1059 that faces the distal-most surface 1055 of the proximal portion 1050a not occupied by the distal portion 1050b of the proximal portion 1050a. As also shown in FIG. 19, the outer surface 1057 also includes a top or distal portion 1052b that, in the example illustrated, is distally tapered. However, a person skilled in the art will appreciate that the second mating element 1052 can have other configurations, as the described techniques are not limited in this respect.

The inner cavity 1053 of the second mating element 1052 can be complementary to the distal portion 1050b of the first mating member 1050 such that the first and second mating elements 1050, 1052 are able to mate when the cavity 1053 receives the distal portion 1050b therein. When the mechanical connection is made in this way between the first and second mating elements 1050, 1052, electrical contacts incorporated into the mating elements 1050, 1052 are also established. For example, as shown in FIG. 19, the distal-most surface 1055 of the proximal portion 1050a of the first mating member 1050 can include a first electrical contact 1060 that is configured to couple with a second electrical 1062 contact formed on the proximal surface of the stepped element 1059. The first electrical contact 1060 can include conductive rings and the second electrical 1062 can include complementary contacts, such as, for example, spring-loaded pogo pins. It should be appreciated, however, that the first and second electrical contacts 1060, 1062 can be electrical contacts of any suitable types which can be disposed at various locations of the first and second mating elements 1050, 1052.

The first and second mating elements 1050, 1052 can be held together using the coupling member 1054. The coupling member 1054 can have a variety of configurations and it can couple to the first and second mating elements 1050, 1052 in different ways.

In the embodiment of FIG. 19, the coupling member 1054 has an internal thread 1064 complementary to the thread 1058 formed around the proximal portion 1050a of the first mating element 1050. Thus, after the first and second mating elements 1050, 1052 are mated such that the cavity 1053 receives the distal portion 1050b therein, the coupling member 1054 can be threadably connected to the first mating element 1050. As shown in FIG. 19, the coupling member 1054 also engages a portion of the second mating element 1052. Specifically, in this example, the coupling member 1054 includes, adjacent to a distal end 1054d thereof, a stepped element 1069 configured to engage the stepped element 1059 formed on the second mating element 1052. The stepped elements 1059, 1069 are configured to fittedly engage with one another, or to engage in other manner, such that the coupling member 1054 brings and holds the first and second mating elements 1050, 1052 together when it is desired so.

Accordingly, the first and second mating elements 1050, 1052 and the coupling member 1054 can provide a secure mechanical and electrical connection. The first mating element 1050 can be coupled to a surgical table or other surface and can be connected to a power source, e.g., as shown for first mating element 612 in FIG. 11. The second mating element 1052 can be coupled to a passive arm or to a mounting pole that is, in turn, coupled to the passive or active arm, as shown, e.g., in FIG. 11 for the second mating element 614. Regardless of the specific components on which the first and second mating elements 1050, 1052 are formed, mating between the first and second mating elements 1050, 1052 allows for both mechanical and electrical coupling therebetween. The power from the power source can thus be transmitted to an electromechanical arm and provided to a surgical tool coupled to such arm. When it is desired to reposition the electromechanical arm or disconnect it from the surgical table, the coupling member 1054 can be disconnected from the first and second mating elements 1050, 1052 (e.g., unscrewed) and the mating elements 1050, 1052 can be separated from one another. In this way, simplified assembly and disassembly of the electromechanical arm is achieved.

Figure 20B:
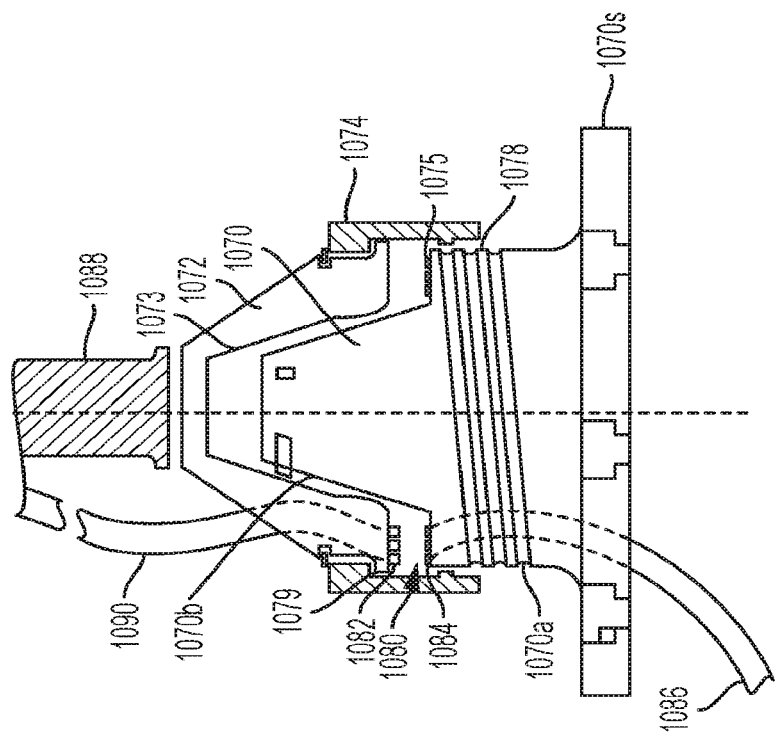
FIG. 20B is a perspective view of the male mating element of FIG. 20A, a female mating element configured to mate therewith, and a coupling element configured to hold the male and female mating elements together.
Figure 20A:
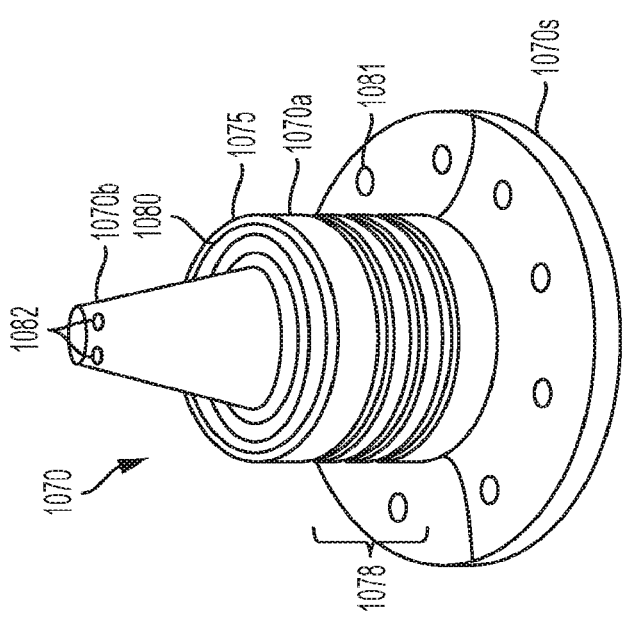
FIG. 20A is a perspective view of one embodiment of a male mating element.

FIGS. 20A and 20B illustrate another embodiment of first and second mating elements 1070, 1072 similar to first and second mating elements 1050, 1052 in FIG. 19. FIG. 20A shows a first mating element 1070 in the form of a male member. Similar to first mating element 1050 in FIG. 19, the first mating element 1070 has support, proximal, and distal portions 1070s, 1070a, 1070b. Each of the portions is generally cylindrical and circular or substantially circular in cross-section, and a circumference of the support portion 1070s is greater than those of the proximal and distal portions 1070a, 1070b, and the circumference of the distal portion 1070b, extending from a distal-most surface 1075 of the proximal portion 1070a, is less than the circumference of the proximal portion 1070a. The support and proximal portions 1070s, 1070a are generally circular in cross-section and can have a substantially constant radius, whereas the distal portion 1070b is tapered distally, as shown in FIGS. 20A and 20B.

The proximal portion 1070a has an outer thread 1078, and the distal-most surface 1075 of the proximal portion has a first electrical contact 1080 in the form of concentric conductive pads or rings disposed on the surface 1075 around the base of the distal portion 1070b forming the "male" portion of the first mating element 1070. An insulating layer 1084 (e.g., a ring or otherwise shaped component) can be disposed underneath the conductive rings, as shown in FIG. 20B. The conductive rings can be spaced equally, or they can be disposed at different distances away from one another on the surface 1075. Furthermore, it should be appreciated that three conductive rings are shown by way of example only, as any suitable number of rings (e.g., one, two, or more than three) can be formed.

As shown in FIG. 20A, the distal portion 1070b includes tolerance or compliance elements 1082, such as two or more buttons or other types of elements of suitable size and shape. Two or more compliance elements 1082 can be disposed around a circumference the conical distal portion 1070b such that they extend above the outer surface thereof. The compliance elements 1082 are configured to be pushed inwards when the first and second mating elements 1070, 1072 are mated. Thus, the compliance elements 1082 facilitate fitting between the first and second mating elements 1070, 1072 when these mating elements are mated. It should be appreciated that the compliance element of any suitable form, size, and shape can be utilized, as the described techniques are not limited in this respect.

The support portion 1070s can include features that are used to mount the first mating element 1070 to a suitable support member, such as an adapter mountable on a surgical table, or other component. In the embodiment illustrated, these features are mounting holes or openings 1081 configured to receive therein a fastening component, such as, for example, a screw. Any suitable number of mounting openings can be formed. Also, a person skilled in the art will appreciate that the first mating element 1070 can be coupled to a support member in a number of different ways, including those not involving any openings formed on the mating element 1070.

The first mating "male" element 1070 can mate with the second mating element 1072 in the form of a female receiver using a coupling element 1074, as shown in FIG. 20B. The coupling element 1074 can be, for example, a coupling nut or other component similar to coupling element 1054 described in connection with FIG. 19, and it is therefore not discussed in detail.

The second mating element 1072 can be coupled in a suitable way to a component 1088 such as an electromechanical surgical arm, as shown in FIG. 20B. The component 1088 can also be a mounting pole coupled to the electromechanical surgical arm (e.g., as shown in FIG. 11). Regardless of the component on which the second mating element 1072 can be disposed, the second mating element 1072 is configured such that an inner cavity 1073 formed therein that is complementary to the distal portion 1070b of the first mating element 1070 can receive therein the distal portion 1070b, as also shown in FIG. 20B. As further shown in FIG. 20B, a proximal-facing surface of a stepped element 1079 formed on a proximal end of the second mating element 1072 includes a second electrical contact 1082 configured to contact and thus establish electrical communication with the first electrical 1080 of the first mating element 1070. As discussed above, the first electrical contact 1080 of the first mating element 1070 is configured to electrically communicate with a power source (e.g., via a cable 1086 coupled to the first electrical contact 1080 and schematically shown in FIG. 20B). The second electrical contact 1082, in turn, is electrically connected to an electromechanical surgical arm, for example, via a cable 1090 coupled thereto, as also schematically shown in FIG. 20B. The cable 1090 can deliver electrical current and control signals to components of the electromechanical surgical arm (e.g., its active portion or arm) and to a surgical instrument coupled to the electromechanical arm. Thus, mating between the first and second mating elements 1070, 1072 causes a contact between the first and second electrical contacts 1080, 1082 to be made, to thereby enable electrical communication between the electromechanical arm and the power source through the first electrical contact 1080.

Figure 21:
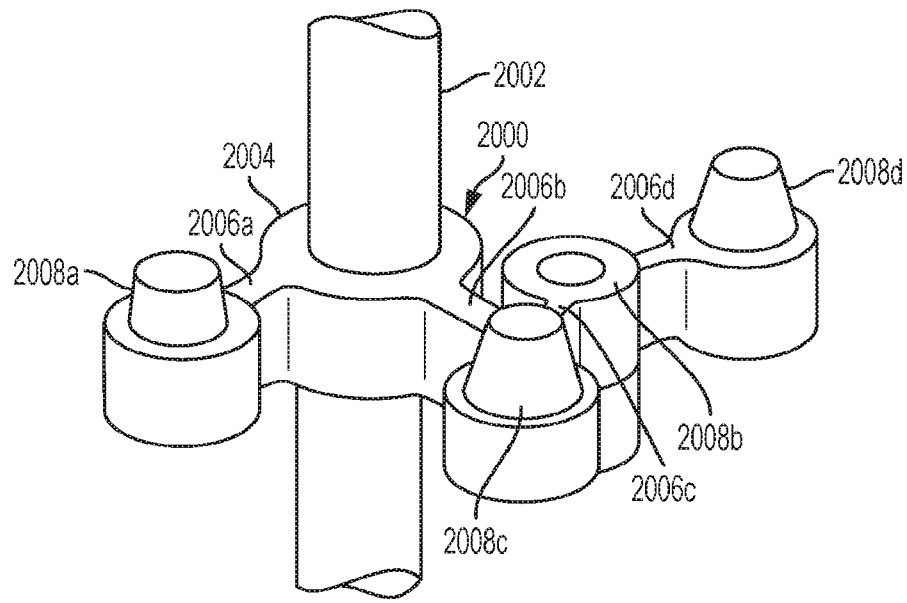
FIG. 21 is a perspective view of an adapter configured to seat more than one electromechanical surgical arm.

As mentioned above, a mating element can be coupled to a mounting pole (or post) or other mounting component configured, in turn, to be mounted on a surgical table or other surface. In some embodiments, the mounting component can be in the form of an adapter or other support structure configured to seat more than one mating element. The adapter can be configured to be mounted on a mounting pole or other component. FIG. 21 illustrates an example of such an adapter 2000 configured to be mounted on a mounting pole 2002. The adapter 2000 can be fitted, screwed, clamped, or snapped to the mounting pole 2002, or it can be otherwise removably secured to the mounting pole 2002. For example, additional fastening component(s) can be used to removably secure the adapter 2000 to the mounting pole 2002. The adapter 2000 can be attached to the mounting pole 2002 such that the adapter 2000 can be repositioned with respect to the mounting pole 2002 in a desired manner.

The adapter 2000 can have a variety of different configurations and it can seat two or more mating elements in various ways and in different orientations with respect to the mounting pole holding the adapter. In the example illustrated, the adapter 2000 includes a base 2004 having a passage or opening that receives therethrough the mounting pole 2002. The adapter 2000 further includes arms 2006*a*, 2006*b* extending from the base 2004 and coupled to mating elements 2008*a*, 2008*b*, respectively, as shown in FIG. 21. The mating elements can be formed as part of the adapter 2000, like in the embodiment described herein. However, in some embodiments, the arms of the adapter can have sockets each configured to receive therein a mating element.

As shown in FIG. 21, the adapter 2000 also has arms 2006*c*, 2006*d* extending at opposite sides from the mating element 2008*b*. The arms 2006*c*, 2006*d* are coupled to mating elements 2008*c*, 2008*d*, respectively. It should be appreciated that the arrangement of the arms 2006*a*, 2006*b*, 2006*c*, 2006*d* is exemplary only, and arms of an adapter can be disposed in different ways. For example, the arms can be disposed along the same axis (with the same or different number of arms disposed at opposite sides of the adapter), disposed around the adapter while being spaced at equal or different distances with respect to each other, or in other suitable ways.

In this example, the mating elements 2008*a*, 2008*c*, 2008*d* are in the form of male members, and the mating element 2008*b* is a female receiver. Regardless of their specific configuration, the mating elements are configured to mate with complementary mating elements that can be disposed on respective electromechanical arms. The mating between the mating elements and their complementary counterpart mating elements also causes an electrical connection to be established therebetween, in accordance with the techniques described herein. A person skilled in the art will appreciate that the adapter can have any number of arms configured to seat any number of mating elements of one or more types. Thus, multiple electromechanical arms can be mounted on a surgical table or other surface in a desired arrangement and such that the mechanical mounting also provides electrical connection between the arms and a power source.

Figure 22:
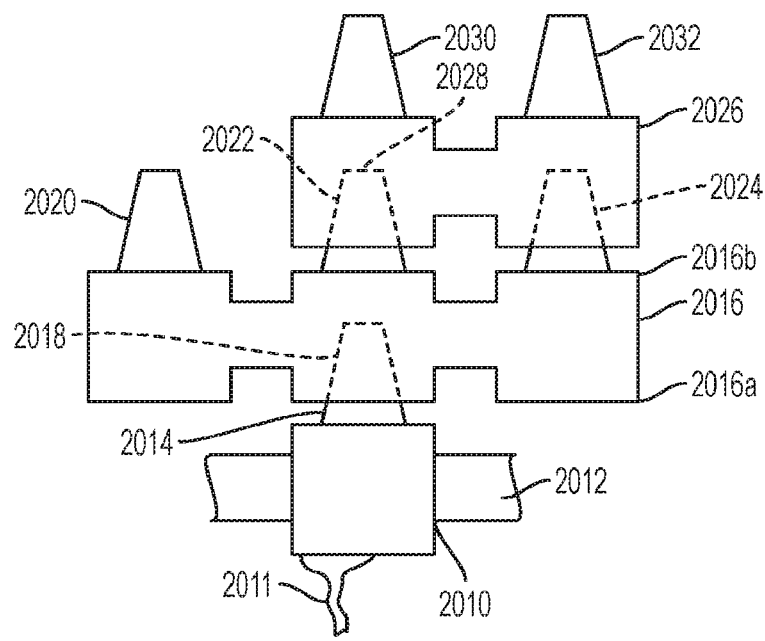
FIG. 22 is a perspective view of stackable adapter structures configured to seat more than one electromechanical surgical arm.

As another way of coupling mating elements to a surgical table or other surface, the mating elements can be coupled to a support member, such as an adapter, such that they are stacked or nested in various ways. FIG. 22 illustrates an example of such an adapter 2010 that can be fixedly or movably coupled to a surgical table. In the example illustrated, the adapter 2010 is coupled to a rail 2012, which can be similar, e.g., to rail 607 (FIG. 11) or rail 627 (FIG. 12). The adapter 2010 can be coupled to a power source (not shown) via a cable 2011. The adapter 2010 can be or can have a mating element 2014 in the form of a male member. The male mating element 2014, in turn, can have a first structure 2016 stacked thereon. The structure 2016 can be disposed at a different plane than the adapter 2010 and the male element 2014.

As shown in FIG. 22, the structure 2016 includes, on one (bottom) side 2016*a* thereof, a mating element 2018 in the form of a female receiver configured to receive therein the male mating element 2014, thereby the structure 2016 is seated over the mating element 2014. On its opposite (top) side 2016*b*, the structure 2016 has male mating elements 2020, 2022, 2024. As further shown in FIG. 22, the male mating element 2022 is able to mate with a complementary female mating element 2028 formed in a second structure 2026 such that the second structure 2026 is stacked over the first structure 2016. The second structure 2026 has two male elements 2030, 2032 formed thereon on the side opposite from the side having the female mating element 2028. In the example of FIG. 22, the structure 2026 can be disposed in a plane different from a plane in which the structure 2016 is positioned.

It should be appreciated that more than two structures can be stacked in the described or similar manner(s). Furthermore, each of the structures can have any number of mating elements of a desired type(s). The structures can be disposed in different planes, and they can be positioned at various angles with respect to each other and with respect to the adapter 2010. The mating elements 2020, 2024, 2030, 2032 can mate with complementary mating elements each formed on an electromechanical arm such that multiple electromechanical arms can be coupled to the stacked structures supported by the adapter 2010. Furthermore, if, for example, the structure 2016 is coupled to a different structure one of the mating element 2020, 2024 can be used to connect to the structure 2016 to that structure. Thus, the mating elements can be configured such that they can be interchangeably used for connecting to another support structure or to have an electromechanical arm mounted thereon. As the structures are stacked by mating between appropriate complementary mating elements, electrical connections are established between the electromechanical arms and the power supply in accordance with the described techniques.

FIGS. 23, 24A, 24B, 24C, and 24D illustrate yet another example of male and female mating elements 2040, 2042 that can mate so as to establish both mechanical and electrical connection therebetween. In this example, the conical, distally tapered male mating element 2040 has a recess or cavity 2044 on a distal or top surface 2040*d* thereof. The cavity 2044 extends proximally into within the mating element 2040 where it is shaped as a stem 2044*s* and a ball 2044*b* extending proximally from the stem 2044*s*, as shown in FIG. 23.

The female mating element 2042, having an inner cavity 2046 that is complementary to the conical male mating element 2040, has an element 2048 extending proximally from a distal or top surface 2042*d* thereof into the inner cavity 2046, as also shown in FIG. 23. In this example, the element 2048 is in the form of a bifurcated stem and ball 2048*s*, 2048*b* extending proximally from the stem 2048*s* such that a region 2049 is formed between the two portions of the bifurcated element 2048.

The element 2048 is formed such that it is accessible from the top surface 2042*d* of the female mating element 2042 via an opening 2050. As shown in FIGS. 24A and 24B, the female mating element 2042 has a cam-lock connector 2052 coupled thereto. The cam-lock connector 2052 is configured to be actuated by rotating a cam 2054 coupled to a body 2053 of the cam-lock connector 2052, as discussed below. The cam-lock connector 2052 can be coupled with the female mating element 2042 such that a portion of the cam-lock connector 2052 extends into the opening 2050 of the female mating element 2042.

To mate the male and female mating elements 2040, 2042, the female mating element 2042 is inserted (e.g., pushed) onto the male mating element 2040 such that the bifurcated stem and ball 2048*s*, 2048*b* of the element 2048 are moved into the cavity 2044 in the male mating element 2040 until the ball 2048*b* reaches the bottom of the cavity 2044 (the ball-shaped portion 2044*b* thereof), as shown in FIG. 24B.

Because of the bifurcated configuration of the element 2048, the ball 2048b can collapse such that it fits through the opening of the cavity 2044. The element 2048 can be fittedly mated with the cavity 2044.

It should be appreciated that the element 2048 having two longitudinal segments is shown by way of example only, as the element 2048 or a similar element can include any suitable number of segments (e.g., three, four, or more than four). For example, the element 2048 can have four segments formed by one longitudinal cut along a longitudinal axis of the element 2048 and another longitudinal cut along the longitudinal axis in a plane perpendicular or otherwise angled with respect to a plane of the first cut.

As another variation, the element 2048 (having two or more segments) can be configured such that the "ball" element extending from the stem 2048s is not a full spherical ball, but two opposed portions of such element along a longitudinal axis thereof are flattened. In this way, when such "partial ball" element is pushed through the cavity 2044, its segments are brought closer together and thus pass through the opening of the cavity 2044.

In the example illustrated, the opening of the cavity 2044 is circular or partially circular. In some embodiments, the opening of the cavity 2044 can be at least partially elliptical such that the stem portion 2044s (FIG. 23) of the element 2048 having two or more segments is at least partially elliptical. The proximal portion of the cavity 2044, which is shaped as the ball 2044b in this example, can have a shape complementary to the shape of the ball 2048b of the element 2048, or it can have other shapes, including irregular shapes.

Furthermore, as a person skilled in the art will appreciate, the stem and ball 2044s, 2044b of the cavity 2044 formed in the male mating element 2040 configured to receive the stem and ball 2048s, 2048b of the element 2048 of the female mating element 2042 are shown by way of example only. The element 2048 and the cavity 2044 can have a variety of other shapes and configurations, and they can have various sizes.

Figure 24C:
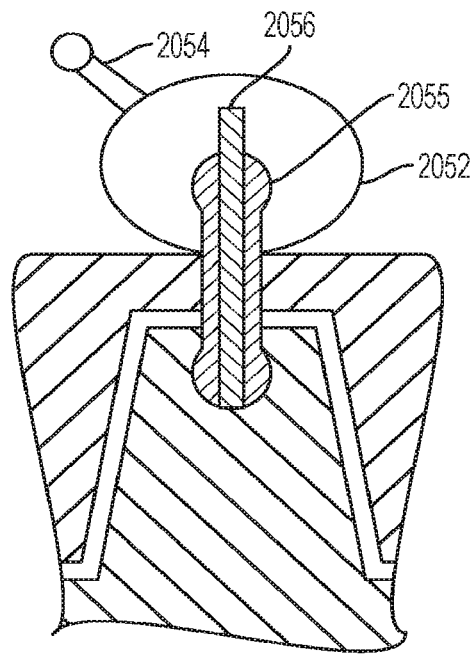
FIG. 24C is a cross-sectional view of the male and female mating element of FIG. 23 shown as initially brought together.

To prevent the element 2048 from backing out of the cavity 2044, a locking pin 2056 or other suitable element can be inserted into the region 2049 of the element 2048, as shown in FIG. 24C. For example, the pin 2056 can be forced into the region 2049 such that the two bifurcated portions of the element 2048 are pushed apart (or prevented from collapsing down), and the pin 2056 is firmly lodged in place. Also, although not shown, the region 2049 can have features that help to retain the pin 2056 within the region 2049. As shown in FIG. 24C, the cam-lock connector 2052 has an opening 2055 formed therein that is configured to receive the pin 2056 therein.

Figure 24D:
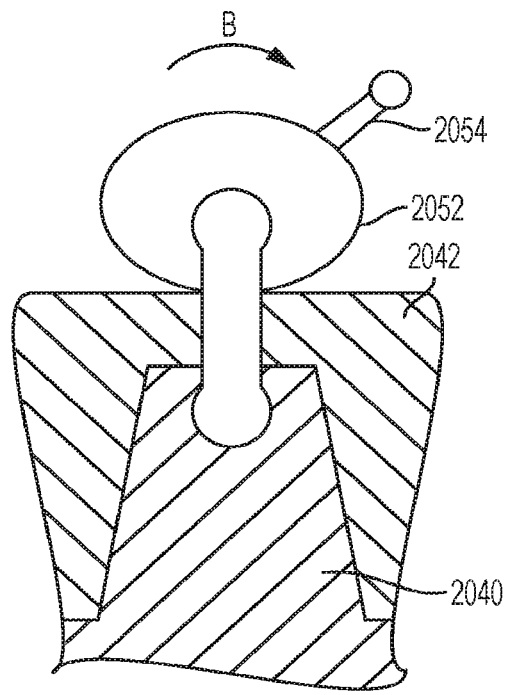
FIG. 24D is a cross-sectional view of the male and female mating element of FIG. 23 shown as brought together in a final coupling.

At a point when the pin 2056 is inserted into the element 2048 formed in the female mating element 2042, the male and female mating elements 2040, 2042 are held together, but are not yet brought into a close contact, as shown in FIG. 24C. The cam 2054 of the cam-lock connector 2052 is then moved in a direction B to actuate the cam-lock connector 2052, as also shown in FIG. 24C. In the example illustrated, the cam-lock connector 2052 is configured such that, when the cam 2054 is rotated, the pin 2056 is urged (e.g., pulled up) to bring the mating elements 2040, 2042 into a close contact with one another, as shown in FIG. 24D (where the pin 2056 is not shown). In this way, the male mating element 2040 is wedged tightly against the female mating element 2042. Similar to the examples described herein, the mechanical coupling between the mating elements 2040, 2042 causes electrical contacts formed on the mating elements 2040, 2042 to make contact to thereby establish electrical communication between the mating elements.

A person skilled in the art will appreciate that the cam-lock connector 2052 can have any suitable configuration and that it is shown in FIGS. 24A-24D by way of example only. Also, the cam-lock connector 2052 can have various other features not shown herein. For example, it can have an over-center feature (not shown) that prevents the arm 2054 from moving out of its position, once it is actuated to cause the pin 2056 to bring the mating elements 2040, 2042 close together. As another example, the element 2048 can include a screw thread, and a nut associated with the element 2048 can be used to manipulate the screw thread to bring the mating elements 2040, 2042 together. A person skilled in the art will appreciate that other suitable mechanisms can be used additionally or alternatively.

The connectors described herein formed by mating between various types of complementary mating elements can include additional components that facilitate or improve operation of the connectors in various ways. For example, in some embodiments, one or both of the mating elements can be associated with one or more connector blanking elements. The blanking elements can be used to plug a mating element when an electrical contact formed on that mating element is not being used to carry an electrical signal. The blanking elements prevent dirt, fluids and contaminants from entering the mating element and thus degrading the quality of electrical connection when the electrical contact of the mating element is used to establish such connection.

The blanking elements can have various configurations, as the described techniques are not limited in this respect. For example, a blanking element can be a guard cover configured to be placed over a mating element in the form of a male element. The guard cover can be configured such that it fits over and protects the male mating element when it is not in use. As an example, the guard cover can be formed from a deformable material (e.g., plastic, metal, or any combination of materials) and it can be snap fitted over the male mating element such that it is compressed over and thus plugs one or more electrical contacts. The electrical contacts can be, for example, pogo pins or other spring-loaded electrical contacts. The cover can have uniform properties throughout, or it can have segments configured such that each segment can contact different regions of the mating element having one or more electrical contacts formed thereon. It should be appreciated that the blanking element can have any other configuration. For example, it can include a blanking shell, blanking plate, blanking plug, or any other element(s) configured to be removably disposed over a mating element to protect its electrical contact(s) when the mating element is not in use. Blanking element for female, male, or other types of mating elements can be utilized. Regardless of the specific configuration of the blanking element used, it can help to extend lifetime of a mating element and can reduce maintenance costs.

Furthermore, one or both of complementary mating elements described herein can be associated with sealing elements, such as one or more O-rings, lip seals, labyrinth seals, or other sealing elements. The sealing elements can protect the mating elements from dirt and other contaminants, and can accommodate for ventilation and, in some cases, drainage of connectors formed by the mating elements when they are coupled to one another.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described techniques based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system, comprising:
a support member having a first mating element that is one of a male member and a female receiver, the first mating element having formed thereon a first electrical contact configured to electrically communicate with a power source;
an electromechanical surgical arm having a tool interface configured to receive and support a surgical tool and a second mating element configured to mate to the first mating element, the second mating element having formed thereon a second electrical contact configured to contact the first electrical contact when the first and second mating elements are mated and to thereby enable electrical communication between the electromechanical surgical arm and the power source through the first electrical contact; and
at least one tolerance element formed on at least one of the first mating element and the second mating element, the at least one tolerance element being configured to provide at least one of axial and radial compliance between the first mating element and the second mating element, wherein the at least one tolerance element is comprised of at least one deformable element.

2. The surgical system of claim 1, wherein the electromechanical surgical arm comprises an active arm portion configured to receive and support the surgical tool, and a passive arm portion removably coupled to the active arm portion and having the second mating element formed thereon.

3. The surgical system of claim 1, wherein the first electrical contact is in electrical communication with a controller.

4. The surgical system of claim 3, wherein the first electrical contact is configured to communicate power and control signals generated by the controller.

5. The surgical system of claim 1, wherein the electromechanical surgical arm comprises a mounting pole having the second mating element disposed thereon.

6. The surgical system of claim 1, wherein the first and second electrical contacts are formed such that, when the first and second mating elements are in at least one of axial or radial compliance with respect to each other, the first and second electrical contacts provide an electrical coupling between the support member and the electromechanical surgical arm.

7. The surgical system of claim 1, wherein the support member is configured to be removably attached to a surgical table.

8. The surgical system of claim 1, further comprising a coupling element configured to secure the first mating element and the second mating element.

9. The surgical system of claim 8, wherein the coupling element comprises a nut.

10. The surgical system of claim 9, wherein the nut is attached to at least one of the first mating element and the second mating element via a threaded connection.

11. The surgical system of claim 1, wherein the first and second mating elements are configured to couple to provide the mechanical and electrical coupling between the support member and the electromechanical surgical arm.

12. A method of using a surgical system, comprising:
establishing a mechanical and electrical connection between a first mating element formed on a support member having a first electrical contact configured to electrically communicate with a power source and a second mating element having a second electrical contact and formed on an electromechanical surgical arm configured to receive and support a surgical tool, wherein the connection is established such that a mechanical coupling between the first and second mating elements causes electrical connection to be established between the first and second electrical contacts, which causes electrical communication to be established between the electromechanical surgical arm and the power source through the first electrical contact; and
operating the electromechanical surgical arm via the electrical communication established between the electromechanical surgical arm and the power source,
wherein at least one of the first mating element and the second mating element includes at least one tolerance element formed thereon and configured to provide at least one of axial and radial compliance between the first mating element and the second mating element, the at least one tolerance element is comprised of an elastomeric element or at least one deformable element.

13. The method of claim 12, wherein the first mating element is a male member, and the second mating element is a female receiver, and wherein the male member and the female receiver are configured to mate to each other.

14. The method of claim 12, wherein the electromechanical surgical arm comprises an active arm portion configured to receive and support the surgical tool, and a passive arm portion removably coupled to the active arm portion and having the second mating element formed thereon.

15. The method of claim 12, wherein the first mating element is a female receiver and the second mating element a male member, and wherein the male member and the female receiver are configured to mate to each other.

16. A method of using a surgical system, comprising:
    establishing a mechanical and electrical connection between a first mating element formed on a support member having a first electrical contact configured to electrically communicate with a power source and a second mating element having a second electrical contact and formed on an electromechanical surgical arm configured to receive and support a surgical tool, wherein the connection is established such that a mechanical coupling between the first and second mating elements causes electrical connection to be established between the first and second electrical contacts, which causes electrical communication to be established between the electromechanical surgical arm and the power source through the first electrical contact;
    rotating a coupling nut to reversibly secure the first mating element and the second mating element together; and
    operating the electromechanical surgical arm via the electrical communication established between the electromechanical surgical arm and the power source.

17. The method of claim 16, wherein the first mating element is a male member, and the second mating element is a female receiver, and wherein the male member and the female receiver are configured to mate to each other.

18. The method of claim 16, wherein the electromechanical surgical arm comprises an active arm portion configured to receive and support the surgical tool, and a passive arm portion removably coupled to the active arm portion and having the second mating element formed thereon.

19. The method of claim 16, wherein the first mating element is a female receiver and the second mating element a male member, and wherein the male member and the female receiver are configured to mate to each other.

* * * * *